United States Patent [19]

Zama et al.

[11] Patent Number: 4,822,786

[45] Date of Patent: Apr. 18, 1989

[54] CEPHALOSPORIN COMPOUNDS, AND ANTIBACTERIAL AGENTS

[75] Inventors: Yoshiyuki Zama, Nagareyama; Nobuo Ishiyama, Washinomiya; Tsuneo Saita, Tokyo; Takanobu Naito, Funabashi; Masao Hirose, Iwai; Masaaki Yokoyama, Tokyo; Taiji Asano, Fukuoka; Hisato Senda, Tokyo; Keiji Sekine, Omiya; Shigeru Sanai, Wako, all of Japan

[73] Assignee: Kaken Pharmaceutical Co., Ltd., Tokyo, Japan

[21] Appl. No.: 63,077

[22] Filed: Jun. 17, 1987

[30] Foreign Application Priority Data

Jul. 1, 1986 [JP] Japan ................... 61-152706
Aug. 18, 1986 [JP] Japan ................... 61-191590

[51] Int. Cl.$^4$ ................... C07D 501/38; A61K 31/545
[52] U.S. Cl. ................... 514/202; 514/203; 514/206; 540/222; 540/225; 540/227
[58] Field of Search ................... 540/225, 222, 227; 514/202, 203, 206

[56] References Cited

U.S. PATENT DOCUMENTS 4,616,081 10/1986 Nishikipo et al. ................... 540/222

FOREIGN PATENT DOCUMENTS 86187 7/1981 Japan.
49382 3/1983 Japan.
167576 9/1984 Japan.
219282 12/1984 Japan.

OTHER PUBLICATIONS

Chem. Abst., vol. 88, 22947, p. 642 (1978).
Chem. Abst., vol. 93, 168281, pp. 681 and 682, Heterocycles 1980.

*Primary Examiner*—Nicholas S. Rizzo
*Attorney, Agent, or Firm*—Oblon, Fisher, Spivak, McClelland & Maier

[57] ABSTRACT

A cephalosporin compound having the formula:

wherein $R_1$ is a hydrogen atom, a halogen atom, a methoxy group, a substituted or unsubstituted vinyl group, or —$CH_2$—A wherein A is a hydrogen atom, an azido group, an acyloxy group, a carbamoyloxy group, a subsituted or unsubstituted heterocyclic group (wherein the hetrocyclic ring is a 5- or 6-membered heterocyclic ring having from 1 to 4 oxygen, nitrogen or sulfur atoms), or a substituted or unsubstituted heterocyclic thio group (wherein the heterocyclic ring is a monocyclic or bicyclic heterocyclic ring having from 1 to 5 oxygen, nitrogen or sulfur atoms), or a pharmaceutically acceptable salt thereof.

7 Claims, No Drawings

CEPHALOSPORIN COMPOUNDS, AND ANTIBACTERIAL AGENTS

The present invention relates to novel cephalosporin compounds, processes for their preparation, antibacterial agents containing them and novel intermediate compounds for the preparation thereof.

A number of cephalosporin antibiotics including cefazolin and cephalotin are known. However, none of cephalosporin antibiotics are fully satisfactory with respect to the antibacterial activities particularly against Pseudomonas aeruginosa among gram-negative bacteria.

The present inventors have found that by the introduction of a novel substituent at the 7-position of the cephem ring, it is possible to obtain a cephalosporin compound having remarkable antibacterial activities against both gram-positive bacteria and gram-negative bacteria, particularly against Pseudomonas aeruginosa. The present invention is based on such a discovery.

The present invention provides a cephalosporin compound having the formula:

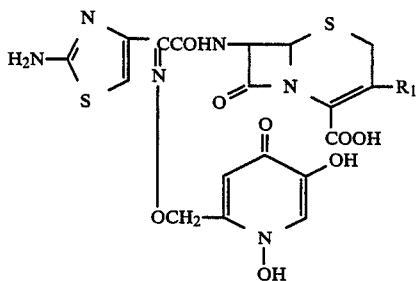

wherein $R_1$ is a hydrogen atom, a halogen atom, a methoxy group, a substituted or unsubstituted vinyl group, or —$CH_2$—A wherein A is a hydrogen atom, an azido group, an acyloxy group, a carbamoyloxy group, a substituted or unsubstituted heterocyclic group (wherein the heterocyclic ring is a 5- or 6-membered heterocyclic ring having from 1 to 4 oxygen, nitrogen or sulfur atoms), or a substituted or unsubstituted heterocyclic thio group (wherein the heterocyclic ring is a monocyclic or bicyclic heterocyclic ring having from 1 to 5 oxygen, nitrogen or sulfur atoms), or a pharmaceutically acceptable salt thereof.

Now, the present invention will be described in detail with reference to the preferred embodiments.

The heterocyclic group for A includes a substituted or unsubstituted tetrazolyl group. Likewise, the heterocyclic thio group for A may be a substituted or unsubstituted thiazolylthio, isothiazolylthio, thiadiazolylthio, triazolylthio, triazinylthio, tetrazolylthio, triazolopyrimidinylthio, 1-substituted pyridinium-4-ylthio or 2,3-cyclopenteno-1-substituted pyridinium-4-ylthio group.

The thiadiazolylthio group may be, for example, a 1,3,4-thiadiazolylthio group, a 1,2,3-thiadiazolylthio group, or a 1,2,4-thiadiazolylthio group. The triazolylthio group may be, for example, a 1H-1,2,3-triazolylthio group, a 4H-1,3,4-triazolylthio group, or a 2H-1,2,4-triazolylthio group. Likewise, the triazolopyrimidinylthio group may be, for example, an s-triazolo[1,5-a]pyrimidinylthio group, or a 1H-triazolo[4,5-e]pyrimidinylthio group.

Further, the substituted on the heterocyclic rings may be, for example, a lower alkyl group, a carboxymethyl group, a lower alkoxycarbonylmethyl group, a hydroxy-(lower)alkyl group, a di-(lower)alkylamino-(lower)alkyl group, a carboxyl group, a hydroxyl group, an oxo group, or an amino group.

Now, specific examples of the compound of the present invention will be given, but it should be understood that the present invention is not limited to such specific compounds.

(6R, 7R)-7-[(Z)-2-(2-aminothiazol-4-yl)-2-(1,5-dihydroxy-4-pyridon-2-ylmethoxyimino)acetamido]-3(1,2,3-thiadiazol-5-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(2-carboxy-5-methyl-s-triazolo[1,5-a]pyrimidin-7-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(1-methyl-1H-tetrazol-5-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3[1-(2-hydroxyethyl)-1H-tetrazol-5-ylthiomethyl]-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(1-carboxymethyl-1H-tetrazol-5-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-[1-(2-dimethylaminoethyl)-1H-tetrazol-5-ylthiomethyl]-3-cepham-4-carboxylic acid.

(6R, 7R)-7-[(Z)-2-(2-aminothiazol-4-yl)-2-(1,5-dihydroxy-4-pyridon-2-ylmethoxyimino)acetamido]-3-(1,3,4-thiadiazol-5-ylthiomethyl)-3-cephem-4carboxylic acid.

(6R, 7R)-7-[(Z)-2-(2-aminothiazol-4-yl)-2-(1,5-dihydroxy-4-pyridon-2-ylmethoxyimino)acetamido]-3-(2-methyl-1,3,4-thiadiazol-5-ylthiomethyl)-3-cephem-4-carboxylic acid.

(6R, 7R)-7-[(Z)-2-(2-aminothiazol-4-yl)-2-(1,5-dihydroxy-4-pyridon (1,2,3-triazol-5-ylthiomethyl)-3-cephem-4carboxylic acid.

(6R, 7R)-7-[(Z)-2-(2-aminothiazol-4-yl)-2-(1,5-dihydroxy-4-pyridon-2-ylmethoxyimino)acetamido]-3-(1,2,5,6-tetrahydro-2-methyl-5,6-dioxo-as-triazin-3-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(5-ethoxycarbonylmethyl-4-methylthiazol-2-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-(4-carboxy-3-hydroxyisothiazol-5-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(acetoxymethy- 3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-vinyl-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-[(5-methyl-2H-tetrazol-2yl)methyl]-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-(5-carboxymethyl-4-methylthiazol-2-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3-(1-methylpyridinium-4-ylthiomethyl)-3-cephem-4-carboxylate.

(6R, 7R)-7-[(Z)-2-(2-aminothiazol-4-yl)-2-(1,5-dihydroxy-4-pyridon-2-ylmethoxyimino)acetamido]-3-(2,3-cyclopenteno-1-methylpyridinium-4-ylthiomethyl)-3-cephem-4-carboxylate.

Sodium salt of (6R, 7R)-7-[(Z)-2-(2-aminothiazol-4-yl)-2-(1,5-dihydroxy-4-pyridon-2-ylmethoxyimino)acetamido]-3-(1-carboxymethylpyridinium-4-ylthiomethyl)-3-cephem-4-carboxylic acid.

Sodium salt of (6R, 7R)-7-[(Z)-2-(2-aminothiazol-4yl)-2-(1,5-dihydroxy-4-pyridon-2-ylmethoxyimino)acetamido]-3-(1-carboxymethyl-2,3-cyclopentenopyridinium- 4-ylthiomethyl)-3-cephem-4-carboxylic acid.

(6R, 7R)-7-[(Z)-2-(2-aminothiazol-4-yl)-2-(1,5-dihydroxy-4-pyridon-2-ylmethoxyimino)acetamido]-3(1-t-butoxycarbonylmethylpyridinium-4-ylthiomethyl)-3-cephem-4-carboxylate.

(6R, 7R)-7-[(Z)-2-(2-aminothiazol-4-yl)-2-(1,5-dihydroxy-4-pyridon-2-ylmethoxyimino)acetamido]-3(1-t-butoxycarbonylmethyl-2,3-cyclopentenopyridinium-4-ylthiomethyl)-3-cephem-4-carboxylate.

(6R, 7R)-7-[(Z)-2-(2-aminothiazol-4-yl)-2-(1,5-dihydroxy-4-pyridon-2-ylmethoxyimino)acetamido]-3-(5-metyl-s-triazolo[1,5-a]pyrimidin-7-ylthiomethyl)-3-cephem-4-carboxylic acid.

The compounds of the formula I of the present invention may be used as they are or in the form of their salts. The salts are pharmaceutically acceptable nontoxic salts with an acid or with a base. The salts with an acid include salts with an inorganic acid such as a hydrogen halide acid (e.g. hydrochloric acid or hydrobromic acid) or sulfuric acid, and salts with an organic acid such as fumalic acid or citric acid. The salts with a base include an alkali metal salt such as a sodium salt or a potassium salt, and salts with an organic base such as an ammonium salt, a dicyclohexylamine salt, a triethylamine salt, an ethanolamine salt, an ornithine salt or a lysine salt. Further, the compounds of the formula I of the present invention have (Z)-isomer and (E)-isomer because of the partial structure represented by the formula:

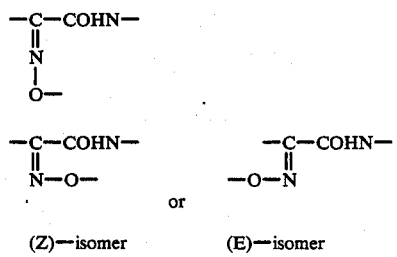

Such isomers and third mixtures are included in the scope of the present invention.

Furthermore, the compounds of the formula I of the present invention have the following keto and enol tautomeric isomers because of the partial structure represented by the formula:

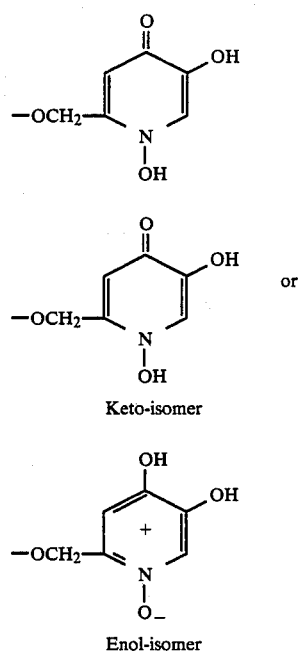

Such isomers and their mixtures are included in the scope of the present invention. For the convenience sake, however, the compounds will be named by the keto-form.

The compounds of the formula I of the present invention may be prepared by various processes. Typical processes will be described below.

Process 1

The compound of the formula I of the present invention can be prepared by reacting a compound having the formula:

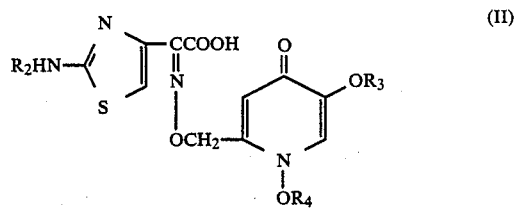

wherein $R_2$ is a hydrogen atom or an amino-protecting group, and each of $R_3$ and $R_4$ is a hydrogen atom or a hydroxyl-protecting group, or a reactive derivative thereof, with a compound having the formula:

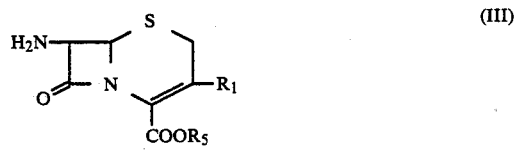

wherein $R_1$ is as defined above, and $R_5$ is a hydrogen atom or a carboxyl-protecting group, to form a compound having the formula:

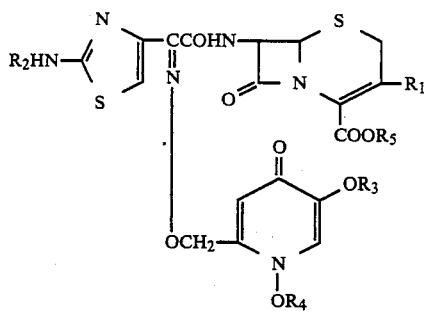

wherein $R_1$, $R_2$, $R_3$, $R_4$ and $R_5$ are as defined above, and, if necessary, removing the amino-protecting group, the hydroxyl-protecting group and the carboxyl-protecting group in the compound of the formula IV.

The amino-protecting group for $R_2$ includes a tri-lower alkylsilyl group such as a trimethylsilyl group, an acyl group such as a formyl group, a chloroacetyl group, a p-methoxybenzyloxycarbonyl group, a t-butoxycarbonyl group, a 2,2,2-trichloroethoxycarbonyl group, or a p-nitrobenzyloxycarbonyl group, and an aralkyl group such as a benzyl group, a p-methoxybenzyl group, a p-nitrobenzyl group, a benzhydryl group (a diphenylmethyl group) or a trityl group (a triphenylmethyl group). The hydroxyl-protecting group for $R_3$ and $R_4$ includes a tri-lower alkylsilyl group such as a trimethylsilyl group, an acyl group such as a formyl group, an acetyl group, a propionyl group, a methoxyacetyl group, or a methoxypropionyl group, an aralkyl group such as a benzyl group, a p-methoxybenzyl group, a p-nitrobenzyl group, a benzhydryl group, or a trityl group, a methoxymethyl group, an allyl group, and a pyranyl group. The carboxyl-protecting group for $R_5$ includes a tri-lower alkylsilyl group such as a trimethylsilyl group, a benzhydryl group, a β-methylsulfonylethyl group, a phenacyl group, a p-methoxybenzyl group, a t-butyl group, a p-nitrobenzyl group, and a 2,2,2-trichloroethyl group.

In the above process, each reaction is conducted usually in a solvent at a reaction temperature of from $-50°$ to $50°$ C. There is no particular restriction as to the solvent so long as it is inert to the reaction. Preferably, however, acetonitrile, dimethyl sulfoxide, dichloromethane, dichloroethane, chloroform, ethyl ether, ethanol, dioxane, tetrahydrofuran, acetone, ethyl acetate, dimethylformamide or dimethylacetamide is used. These solvents may be used alone or in combination as a proper mixture. Further, different solvents may be employed for the respective reaction stages.

The compound of the formula II may be used in the form of a free carboxylic acid, or may be used for the reaction in the form of a salt or in the form of a reactive derivative of the carboxylic acid. A suitable reactive derivative includes an acid halide (such as an acid chloride or an acid bromide), an active ester (such as a benzotriazole ester, a cyanomethyl ester, a nitrophenyl ester, an N-hydroxysuccinimide ester or an N-hydroxyphthalimide ester), a mixture of acid anhydrides (such as a mixture of acid anhydrides with ethoxycarboxylic acid, isobutoxycarboxylic acid and trimethyl acetate), an active amide, and an active azide. When the compound of the formula II is used in the form of a free carboxylic acid, it is preferred to employ a condensation agent such as N,N'-dicyclohexylcarbodiimide or N,N'-diethylcarbodiimide. Depending upon the type of the reactive derivative of the carboxylic acid to be used, it may be suitable in some cases to conduct the reaction in the presence of a base in order to carry out the reaction smoothly. As a base to be used in such a case, there may be mentioned an inorganic base such as sodium hydrogen carbonate or potassium carbonate, or an organic base such as trimethylamine, triethylamine, dimethylaniline, pyridine, N-methylmorpholine, dicyclohexylamine or diethylamine. The removal of the protective groups may be conducted by common methods based on the properties of the protective groups for the amino, hydroxyl or carboxyl groups to remove the amino protecting group $R_2$, hydroxyl-protecting groups $R_3$ and $R_4$ and carboxyl-protecting group $R_5$ in the formula IV.

Process 2

Among the compounds of the present invention, those represented by the formula:

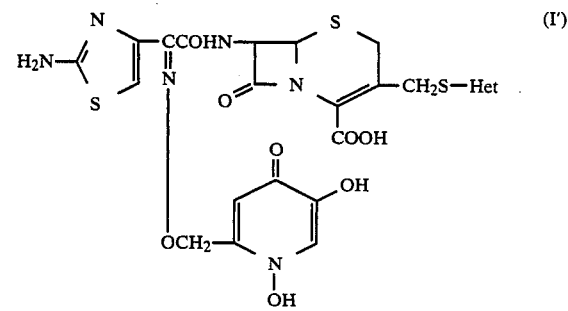

wherein Het is a substituted or unsubstituted heterocyclic group (wherein the heterocyclic ring is a monocyclic or bicyclic heterocyclic ring having from 1 to 5 oxygen, nitrogen or sulfur atoms), can be prepared by reacting a compound having the formula:

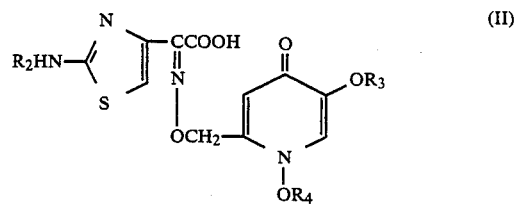

wherein $R_2$ is a hydrogen atom or an amino-protecting group, and each of $R_3$ and $R_4$ is a hydrogen atom or a hydroxyl-protecting group, with a compound having the formula:

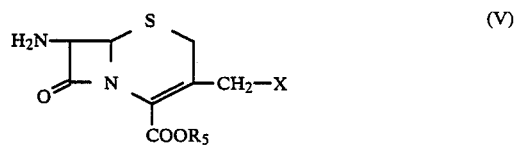

wherein $R_5$ is a hydrogen atom or a carboxyl-protecting group, and X is a chlorine atom, a bromine atom, an iodine atom or an acetoxy group, to form a compound having the formula:

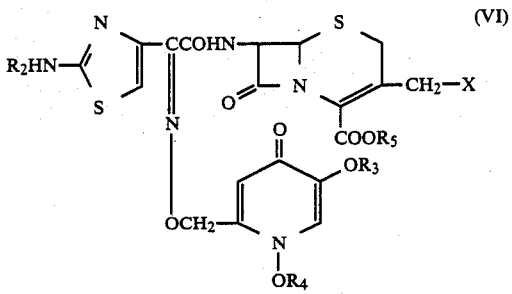

wherein $R_2$, $R_3$, $R_4$, $R_5$ and X are as defined above, and then reacting the compound of the formula VI with a compound having the formula:

wherein Het is as defined above, to form a compound having the formula:

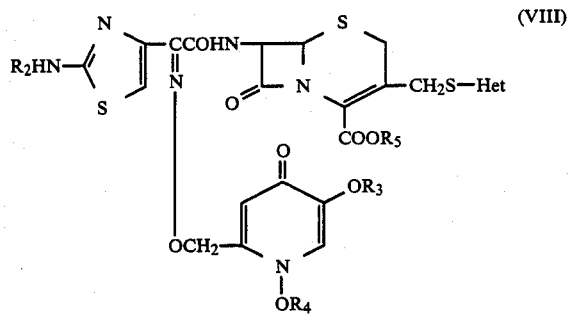

wherein $R_2$, $R_3$, $R_4$, $R_5$ and Het are as defined above, and, if necessary, removing the amino-protecting group, the hydroxyl-protecting group and the carboxyl-protecting group in the compound of the formula VIII.

In the above process, each reaction is conducted usually in a solvent at a reaction temperature of from −50° to 50° C. There is no particular restriction as to a solvent so long as it is inert to the respective reactions. Preferably, however, acetonitrile, dimethylsulfoxide, dichloromethane, dichloroethane, chloroform, ethyl ether, methanol, dioxane, tetrahydrofuran, acetone, ethyl acetate, dimethylformamide or dimethylacetamide is used. These solvents may be used alone or in a combination as a proper mixture. Further, different solvents may be used for the respective reaction stages.

The compound of the formula VII may be used in the free form, but it may advantageously be used in the form of an alkali metal salt such as a sodium salt or a potassium salt. The reaction time varies depending upon the starting material, solvent, etc., and is usually suitably selected within a range of a few hours to a few days. The reaction is conducted usually at a pH of from 2 to 8, preferably at a neutral level. In some cases, a quaternary ammonium salt having a surface active function such as trimethylbenzylammonium bromide or triethylbenzylammonium hydroxide, may be added to the reaction system to conduct the reaction smoothly. Further, in order to prevent the oxidation in air, the reaction may be conducted in an inert atmosphere such as nitrogen, whereby an advantageous results will be obtained.

The removal of the protective groups may be conducted by common methods based on the properties of the protective groups for the amino, hydroxyl or carboxyl groups, to remove the amino-protecting group $R_2$, hydroxyl-protecting groups $R_3$ and $R_4$ and carboxyl-protecting group $R_5$ in the formula VIII.

As shown in Tables 1 and 2 given hereinafter, compounds of the formula I of the present invention exhibit excellent anti-bacterial activities and infection-preventive effects. They show excellent activities against some pathogenic bacteria belonging to gram-positive bacteria. A particularly important feature is that they show remarkable effectiveness against Pseudomonas aeruginosa. Thus, the compounds of the formula I and their salts according to the present invention are useful as anti-bacterial agents or chemical treatment agents for warm blood animals including human beings and domestic animals. They are useful for curing infectious diseases caused by gram-positive bacteria and gram-negative bacteria. They are also useful as additives to animal feeds.

The compounds of the formula I and their salts according to the present invention may be administered orally or non-orally (e.g. intravenous administration, intramuscular administration or hypodermic administration). The dose varies depending upon the age, weight, condition and the degree of disease of the patient. Usually, however, the dose per day is from about 0.2 to about 10 g, preferably from 0.5 to 4.0 g. The compound of the formula I or its salt may be used also as a pharmaceutical drug having a pharmaceutically acceptable vehicle incorporated to be suitable for oral or non-oral administration. The pharmaceutically acceptable vehicle includes gelatin, lactose, fructose, sodium chloride, starch, magnesium stearate, talc, vegetable oil and other pharmaceutical vehicles. The pharmaceutical drug may be a solid formulation such as tablets, granules, capsules, microcapsules or powder, or may be a liquid formulation such as a solution, a suspension or an emulsion. Further, if necessary, an adjuvant, a stabilizer, a wetting agent, an emulsifier or other conventional additives may be incorporated.

Another object of the present invention is to provide an intermediate compound of the formula II useful for the preparation of the compound of the formula I of the present invention.

The intermediate compound of the formula II includes a compound having the formula:

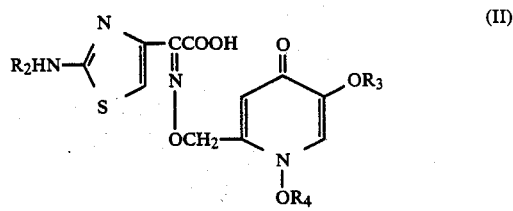

wherein $R_2$, $R_3$ and $R_4$ are as defined above, or its reactive derivative. As a suitable reactive derivative, there may be mentioned, for example, an acid halide (such as an acid chloride or an acid bromide), an active ester (such as benzotriazole ester, cyanomethyl ester, nitrophenyl ester, N-hydroxysuccinimide ester or N-hydroxyphthalimide ester), a mixture of acid anhydrides (such as a mixture of acid anhydrides comprising ethoxycarboxylic acid, isobutoxycarboxylic acid and trimethyl acetate), an active amide, and an active azide.

A typical method for the preparation of the intermediate compound of the formula II of the present invention will be described. A compound of the formula X wherein R₃ is as defined above, is obtained by protecting the phenolic hydroxyl group of kojic acid of the formula IX by a conventional method. This compound of the formula X is treated in a water-containing alcohol with hydroxylamine hydrochloride and sodium acetate at a temperature of from room temperature to 60° C. to obtain a compound of the formula XI. A compound of the formula XII wherein R₄ is as defined above is obtained by protecting the N-oxide of the compound of the formula XI by a conventional method. The compound of the formula XII is reacted with N-hydroxyphthalimide in an anhydrous solvent (such as dioxane, tetrahydrofuran, dimethylformamide or dimethylacetamide) in the presence of triphenylphosphine and azodicarboxylic acid diethyl ester, to obtain a compound of the formula XIII. This compound of the formula XIII is treated with hydrazine to obtain a compound of the formula XIV, which is then reacted with a compound of the formula XV, to obtain an intermediate compound of the formula II.

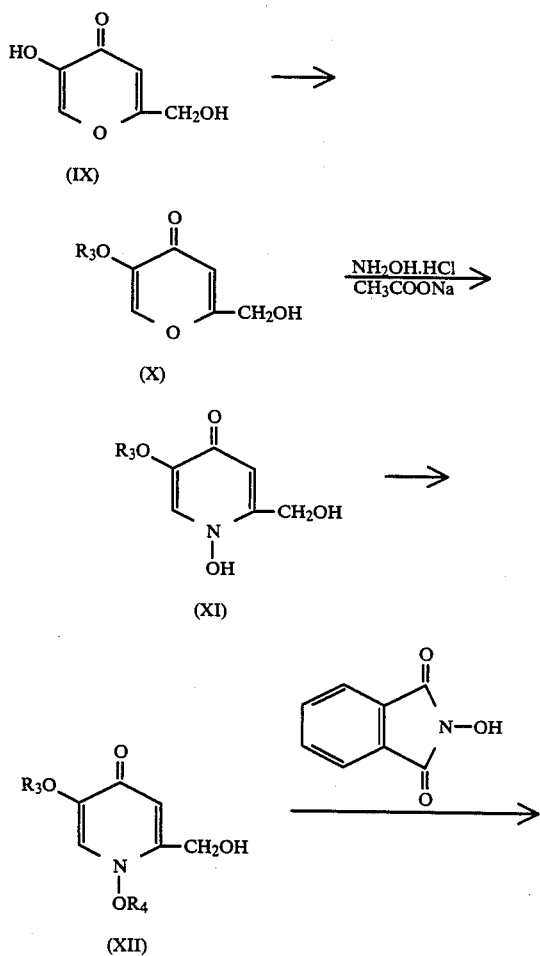

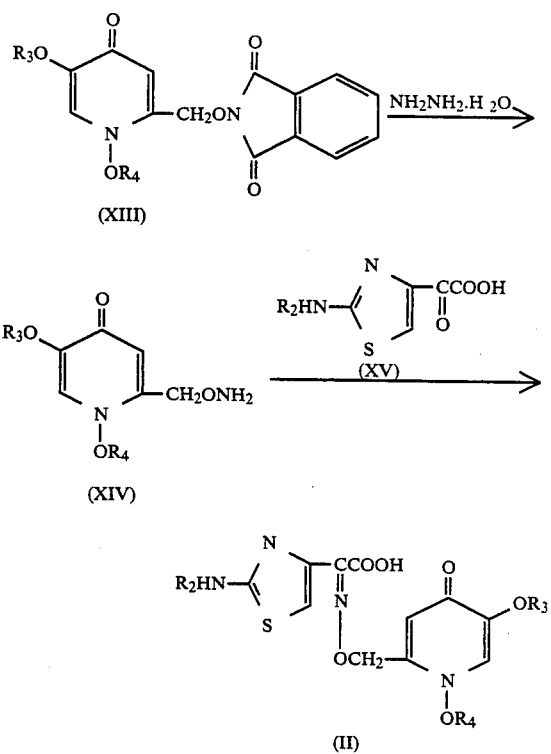

Now, the present invention will be described in further detail with reference to Test Examples, Reference Examples and working Examples. However, it should be understood that the present invention is by no means restricted to such specific Examples.

TEST EXAMPLE 1: Measurement of minimum inhibitory concentration

The minimum inhibitory concentration (M.I.C.) (μg/ml) of each test compound was measured by an agar plate dilution method according to the standard method by Japan Chemical Therapy Academy by using a Muller-Hinton agar culture medium (manufactured by Nissui K.K.). As the test bacteria, *Staphylococus aureus* FDA 209-P JC-1, *Escherichia coli* ML 4707, *Klebsiella pneumoniae* No. 42, *Proteus vulgaris* No. 33, *Serratia marcescens* No. 16-2, *Enterobacter cloacae* Nek 39, *Acinetobacter calcoaceticus* No. 4, Pseudomonas aeruginosa K-13, Pseudomonas aeruginosa Y-1 and *Pseudomonas cepacia* 23 were employed. The results are shown in Table 1.

TABLE 1

| | | | | | | | | | (μg/ml) |
|---|---|---|---|---|---|---|---|---|---|
| | Compound (Example No.) | | | | | | | | |
| Bacteria | 3 | 4 | 5 | 6 | 18 | 19 | CTX | CAZ | CFS |
| S. aureus FDA 209-P JC-1 | 6.25 | 12.5 | 50 | 25 | 6.25 | 12.5 | 3.13 | 12.5 | 3.13 |
| E. coli ML 4707 | 0.05 | 0.1 | ≦0.025 | ≦0.025 | ≦0.025 | 0.05 | ≦0.025 | 0.2 | 50 |

TABLE 1-continued (μg/ml)

| Bacteria | Compound (Example No.) | | | | | | | | |
|---|---|---|---|---|---|---|---|---|---|
| | 3 | 4 | 5 | 6 | 18 | 19 | CTX | CAZ | CFS |
| K. pneumoniae No. 42 | 0.1 | 0.2 | ≦0.025 | 0.05 | 0.05 | 0.1 | 0.1 | 0.39 | >100 |
| P. vulgaris No. 33 | 0.05 | 0.1 | ≦0.025 | 0.05 | 0.1 | 0.2 | 0.05 | 0.1 | — |
| S. marcescens No. 16-2 | 0.78 | 0.39 | 0.39 | 0.39 | 0.78 | 1.56 | 6.25 | 1.56 | >100 |
| E. cloacae Nek 39 | 0.78 | 0.39 | 0.39 | 0.78 | 0.39 | 0.2 | 3.13 | 1.56 | >100 |
| A. calcoaceticus No. 4 | 3.13 | 12.5 | 1.56 | 3.13 | 3.13 | 6.25 | 25 | 6.25 | 50 |
| P. aeruginosa K-13 | 0.39 | 0.2 | 0.1 | 0.2 | 0.78 | 1.56 | 25 | 3.13 | 3.13 |
| P. aeruginosa Y-1 | 0.2 | 0.39 | 0.1 | 0.1 | 0.2 | 0.78 | 12.5 | 1.56 | 1.56 |
| P. cepacia 23 | 0.1 | 0.2 | 0.05 | 0.1 | 0.2 | 0.39 | 3.13 | 1.56 | >100 |

(Inoculated amount of cells: $10^6$ CFU/ml
CTX: cefotaxime;
CAZ: ceftazidime;
CFS: cefsulodin

TEST EXAMPLE 2: Infection-preventive effects

JCL:JCR type male mice of 4 weeks old having a body weight of from 17 to 19 g were used in groups each consisting of from 6 to 10 animals. As test bacteria, Staphyloccocus aureus Smith, Escherichia coli ML 4707, Pseudomonas aeruginosa K-13, and Pseudomonas aeruginosa Y-1 were used. The test bacteria were cultured at 37° C. for 16 hours by using a nutrient broth. Depending upon the respective bacteria, bacterial solutions containing from 0.5 to 5% of mucin (Pseudomonas aeruginosa K-13 and Y-1) or bacterial solutions containing no mucin (Staphyloccocus aureus Smith and Escherichia coli ML 4707) were prepared. The bacterial solutions were intraperitoneally inoculated to mice in an amount 0.5 ml each, and upon expiration of 1 hour, solutions containing test compounds were hypodermically administered in the respective doses. Then, the mice were observed for survival or death for 7 days. From the survival rates during the 7 days, $ED_{50}$ values were obtained by a Probit method. The results are shown in Table 2.

TABLE 2

$ED_{50}$ (mg/kg)

| Bacteria (Inoculated amount) | Compound (Example No.) | | | | | | | | |
|---|---|---|---|---|---|---|---|---|---|
| | 3 | 4 | 5 | 6 | 18 | 19 | CTX | CAZ | CFS |
| S. aureus Smith $7.7 \times 10^7$ cells/mouse | 12 | 8.7 | — | 42 | 2.9 | — | 3.1 | 17 | — |
| E. coli ML 4707 $1.1 \times 10^6$ cells/mouse | 0.11 | 0.16 | 0.12 | 0.13 | 0.034 | 0.077 | 0.095 | 0.73 | >100 |
| P. aeruginosa K-13 $3.0 \times 10^4$ cells/mouse | 9.7 | 12 | 18.9 | 4.6 | 13 | 9.6 | >100 | 31 | 39 |
| P. aeruginosa Y-1 $4.0 \times 10^5$ cells/mouse | 2.6 | 4.0 | — | 1.4 | 2.0 | 7.8 | >200 | 16 | 13 |

EXAMPLE 1

(Z)-2-(2-tritylaminothiazol-4-yl)-2-(1,5-dibenzhydryloxy-4-pyridon-2-ylmethoxyimino)acetic acid

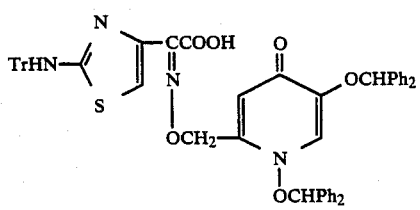

This compound was produced by the following Steps (1) to (5).

(1) 5-benzhydryloxy-2-hydroxymethyl-4-pyrone

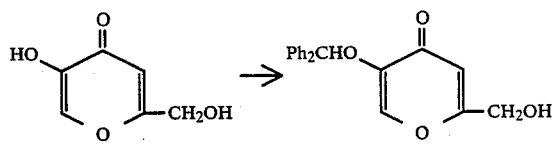

14.2 g (0.1 mol) of kojic acid was added to ethanol (400 ml), and heated to 60° C. and dissolved. After cooling the solution to room temperature, 29.1 g (0.15 mol) of diphenyldiazomethane was added thereto, and the mixture was reacted at room temperature for 18 hours under stirring. The reaction solution was concentrated to dryness, and benzene (300 ml) was added thereto. Then, insolubles were removed by filtration. To the filtrate, water (300 ml) was added, and the precipitates thereby formed were collected by filtration, and washed with benzene to obtain 17.5 g (yield: 56.8%) of the above identified compound.

NMR(CDCl$_3$)δ(ppm): 4.33(2H,s), 6.29(1H,s), 6.49(1H,s), 7.36(10H,s) 7.44(1H,s).

(2) 1-Hydroxy-2-hydroxymethyl-5-benzhydryloxy-4-pyridone

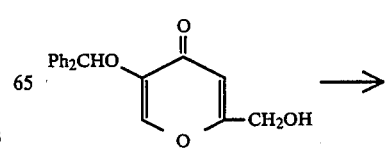

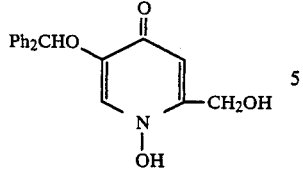

17.5 g (0.0568 mol) of the product of Step (1) was added and dissolved in a mixture of ethanol (60 ml) and water (60 ml). Then, 39.5 g (0.568 mol) of hydroxylamine hydrochloride and 77.2 g (0.568 mol) of sodium acetate trihydrate were added thereto, and the mixture was reacted at 60° C. for 18 hours under stirring. Formed precipitates were collected by filtration, washed sequentially with water, ethanol and ethyl ether, and then dried to obtain 8.1 g (yield: 44.0%) of the above identified compound.

NMR(DMSO-d$_6$)δ(ppm): 2.71(2H,s), 6.65(1H,s), 6.87(1H,s), 7.26–7.63(10H,m), 7.93(1H,s).

(3) 1,5-Dibenzhydryloxy-2-hydroxymethyl-4-pyridone

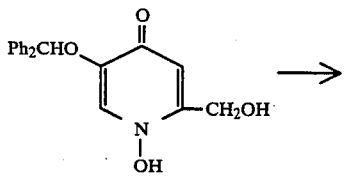

8.1 g (0.0251 mol) of the product of Step (2) was added to dimethylsulfoxide (125 ml) and heated to 100° C. and dissolved. After cooling the solution to room temperature, 5.2 g (0.0375 mol) of potassium carbonate and 5.6 g (0.0375 mol) of sodium iodide and 6.7 ml (0.0375 mol) of benzhydrylchloride were added thereto, and the mixture was reacted at room temperature for 18 hours under stirring. To the reaction solution, ice water was gradually added, and formed precipitates were collected by filtration, washed sequentially with water and ethyl ether/n-hexane (2/1), and dried to obtain 12.3 g (yield: 100%) of the above identified compound.

NMR (CDCl$_3$)δ(ppm): 4.35(2,s), 5.96(1H,s), 6.06(1H,s), 6.55(1H,s), 6.75(1H,s), 7.26(20H,s).

(4) 2-Phthalimidooxymethyl-1,5-dibenzhydryloxy-4-pyridone

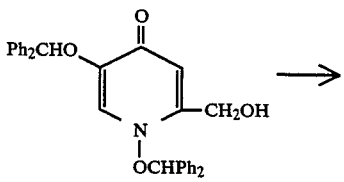

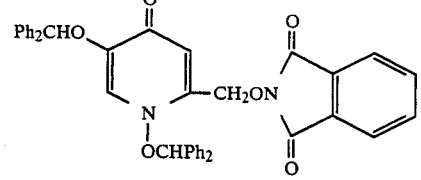

12.3 g (0.0251 mol) of the product of Step (3) was added and dissolved in dimethylformamide (125 ml). Then, dried tetrahydrofuran (250 ml), 4.1 g (0.0251 mol) of N-hydroxyphthalimide and 9.9 g (0.0376 mol) of triphenylphosphine were added thereto. Further, 5.8 ml (0.0377 mol) of diethyl diazodicarboxylate was dropwise added under cooling with ice. The mixture was stirred at the same temperature for 10 minutes, and then ethyl acetate (500 ml) and water (1,500 ml) were added thereto. The ethyl acetate layer was washed with water and a saturated sodium chloride solution, and then dried over anhydrous magnesium sulfate, and then concentrated to dryness. The residue was subjected to silica gel column chromatography and eluted by benzene/ethyl acetate (4/1) to obtain 8.0 g of the above identified compound (yield: 50.2%)

NMR(CDCl$_3$)δ(ppm): 4.97(2H,s), 5.88(1H,s), 6.26(1H,s), 6.73(1H,s) 6.84(1H,s), 7.31(10H,s), 7.44(10H,s), 7.76(4H,s).

(5) (Z)-2-(2-tritylaminothiazol-4-yl)-2-(1,5-dibenzhydryloxy-4-pyridon-2-ylmethoxyimino)acetic acid

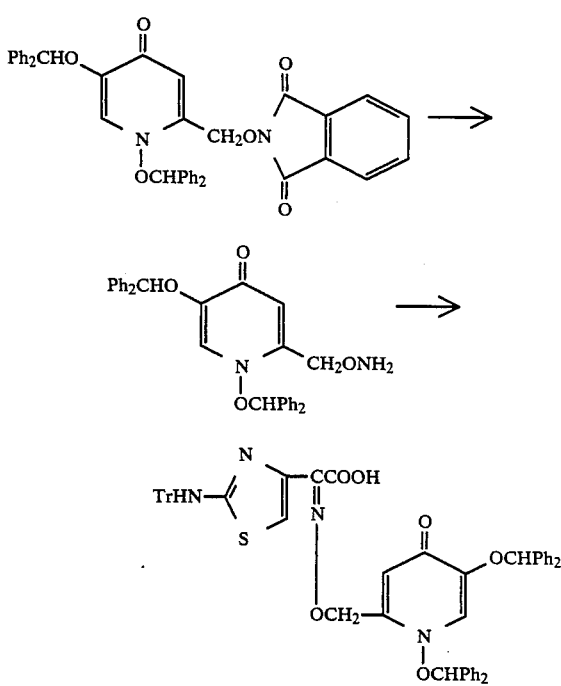

8.0 g (0.0126 mol) of the product of Step (4) was suspended in ethanol (60 ml). Then, 0.629 g (0.0126 mol) of hydrazine monohydrate was added thereto, and the mixture was refluxed for 1 hour. After cooling the reaction solution to room temperature, insolubles were removed by filtration, and the filtrate was concentrated to dryness. The residue was suspended in chloroform (120 ml), and insolubles were removed by filtration. The filtrate was concentrated to dryness and then dissolved in ethanol (60 ml). Then, a chloroform (180 ml) solution of 5.2 g (0.0126 mol) of 2-tritylaminothiazol-4-ylglyoxylic acid was added thereto. This solution was reacted at room temperature for 18 hours under stirring, and then concentrated to dryness. Ethanol and n-hexane were added thereto, and formed precipitates were collected by filtration to obtain 9.5 g (yield: 83.8%) of the above identified compound.

NMR(CDCl$_3$)δ(ppm):
5.02(2H,s), 5.86(1H,s), 6.24(1H,s), 6.53(1H,s), 6.74(1H,s), 6.98(1H,s), 6.89–7.50(35H,bs).

EXAMPLE 2 p-Methoxybenzyl (6R, 7R)-7-[(Z)-2-(2-tritylamino-thiazol-4-yl)-2-(1,5-dibenzhydryloxy-4-pyridon-2-ylmethoxyimino)acetamido]-3-chloromethyl-3-cephem-4-carboxylate

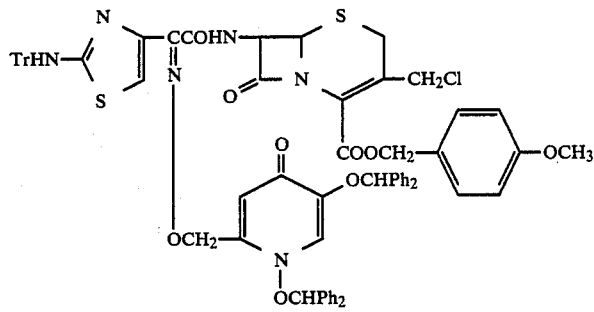

9.38 g (0.01 mol) of p-methoxybenzyl 7-amino-3-chloromethyl-3-cephem-4-carboxylate p-toluene sulfonate was added to a solvent mixture of ethyl acetate (300 ml) and water (100 ml), and 2.18 g (0.026 mol) of sodium hydorgencarbonate was added thereto under cooling with ice. The mixture was stirred for 1 hour. The ethyl acetate layer was washed with a saturated sodium chloride aqueous solution, and dried over anhydrous magnesium sulfate. To this solution, a chloroform solution (500 ml) of 6.25 g (0.00693 mol) of (Z)-2-(2-tritylaminothiazol-4-yl)-2-(1,5-dibenzhydryloxy-4-pyridon-2-ylmethoxyimino)acetic acid obtained in Example 1, 1.0 g (0.00658 mol) of 1-hydroxybenzotriazole and 1.66 g (0.00624 mol) of dicyclohexylcarbodiimide were added under cooling with ice, and the mixture was reacted for 18 hours under stirring. Precipitated insolubles were removed by filtration, and the filtrate was concentrated to dryness. Ethyl acetate (300 ml) was added thereto, and insolubles were removed by filtration. The filtrate was concentrated to dryness, and subjected to silica gel column chromatography and eluted with benzene/ethyl acetate (5/1) to obtain 5.45 g (yield: 62.8%) of the above identified compound.

NMR(CDCl$_3$)δ(ppm):
3.42(2H,bs), 3.75(3H,s), 4.32,4.69(2H,ABq,J=12 Hz), 4.89(1H,d,J=6 Hz), 4.94(2H,s), 5.21(2H,s), 5.74(1H,dd,J=9 Hz, J=7 Hz), 6.05(1H,s), 6.11(1H,s), 6.43(1H,s), 6.71(1H,s), 6.77(1H,s), 7.31(35H,s).

IR(KBr):νc=o 1880 cm$^1$.

EXAMPLE 3

(6R, 7R)-7-[(Z)-2-(2-aminothiazol-4-yl)-2-(1,5-dihydroxy-4-pyridon-2-ylmethoxyimino)acetamido]-3(1,2,3-thiadiazol-5-ylthiomethyl)-3-cephem-4-carboxylic acid

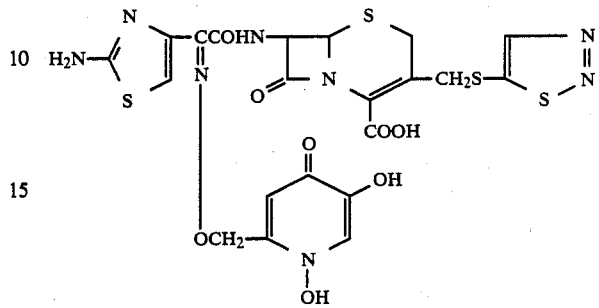

1.242 g (1 mmol) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-chloromethyl-3-cephem-4-carboxylate obtained in Example 2 was dissolved in a solvent mixture of 5 ml of dimethylformamide and 20 ml of ethanol, and cooled with ice. Then, 0.21 g (1.5 mmol) of sodium 1,2,3-thiadiazole-5-thiolate was added to the reaction solution, and the mixture was reacted for 2.5 hours under stirring. The reaction solution was poured into ice, and precipitated crystals were collected by filtration and recrystallized from ethyl acetate/diethyl ether to obtain 1.1 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamide]-3(1,2,3-thiadiazol-5-ylthiomethyl)-3-cephem-4-carboxylate.

1.1 g of the carboxylate thus obtained was added to a mixture of 1.5 ml of anisole and 15 ml of trifluoroacetic acid, and reacted for 2 hours under stirring. The reaction solution was concentrated, and 100 ml of diethyl ether was added thereto. Formed precipitates were collected by filtration to obtain 0.67 g of a trifluoroacetate of the above identified compound.

NMR(DMSO-d$_6$)δ(ppm): 3.60(2H,bs), 4.30(2H,bs), 5.30(3H,m), 5.75(1H,bs), 6.95(1H,s), 7.10(1H,s), 8.15(1H,s), 8.75(1H,s).

IR(KBr):νc=0, 1790cm$^1$.

0.67 g of the above trifluoroacetate was suspended in 20 ml of water, and adjusted to pH 7.0 with a 2% sodium hydrogencarbonate solution. The solution thus obtained was subjected to column chromatography with Amberlite XAD-2 (manufactured by Rohm & Haas Co.). The fraction eluted with methanol/water (4/1) was concentrated and freeze-dried to obtain 0.482 g of a sodium salt of the above identified compound.

EXAMPLE 4

(6R, 7R)-7-[(Z)-2-(2-aminothiazol-4-yl)-2-(1,5-dihydroxy-4-pyridon-2-ylmethoxyimino)acetamido]-3(2-carboxy-5-methyl-s-triazolo[1,5-a]pyrimidin-7-ylthiomethyl)-3-cephem-4-carboxylic acid

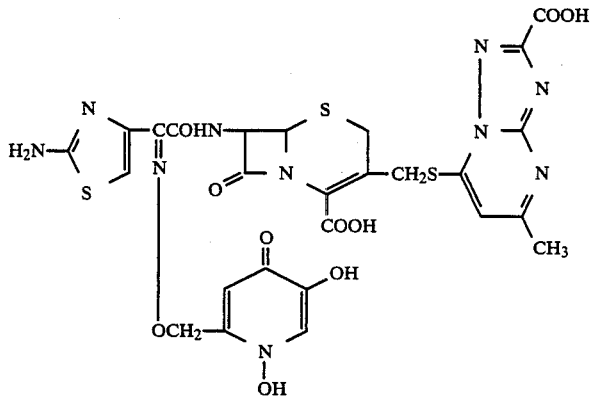

4.465 g (5 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 50 ml of dimethylacetamide. Then, 0.766 g (5 mmol) of 1-hydroxybenzotriazole and 1.03 g (5 mmol) of dicyclohexyl carbodiimide were added thereto under cooling with ice, and the mixture was stirred on ice bath for 1 hour. Then, 3.82 g (6 mmol) of p-methoxybenzyl 7-amino-3-(2-benzhydryloxycarbonyl-5-methyl-s-triazolo[1,5-a]pyrimidin-7-ylthiomethyl)-3-cephem-4-carboxylate was added thereto, and the mixture was reacted at room temperature for 16 hours under stirring. Precipitated insolubles were removed by filtration, and the filtrate was concentrated to dryness and subjected to silica gel column chromatography and eluted with benzene/ethyl acetate (3/1 to ½) to obtain 3.8 g of p-methoxybenzyl (6R, 7R)-7-[(Z)-2-(2-tritylaminothiazol-4-yl-2-(1,5-dibenzhydryloxy-4-pyridon-2-ylmethoxyimino)acetamido]-3-(benzhydryloxycarbonyl-5-methyl-s-triazolo-[1,5-a]-pyrimidin-7-ylthiomethyl)-3-cephem-4-carboxylate.

2.4 g of the carboxylate thus obtained was dissolved in a mixture of 2 ml of anisole and 9 ml of trifluoroacetic acid, and reacted at room temperature for 2 hours. The reaction solution was poured into 150 ml of diethyl ether, and formed precipitates were collected by filtration to obtain 1.252 g of a trifluoroacetate of the above identified compound.

NMR(DMSO-d$_6$)δ(ppm):
2.31(3H,s), 3.69(2H,bs), 5.03(1H,bs), 5.13(2H,s), 5.94(1H,bs), 6.91(1H,s), 7.11(1H,s), 7.38(1H,s), 8.23(1H,s).

IR(KBr):νc=o 1780 cm$^{-1}$.

1.12 g of the above trifluoroacetate was suspended in 50 ml of water and adjusted to pH 7 with a sodium hydrogencarbonate solution. The solution thus obtained was washed with ethyl acetate, and the aqueous phase was subjected to column chromatography with HP-20 (manufactured by Mitsubishi Chemical Industries Limited). The fraction eluted with ethanol/water (4/1) was concentrated and freeze-dried to obtain 0.5 g of a sodium salt of the above identified compound.

EXAMPLE 5

(6R, 7R)-7-[(Z)-2-(2-aminothiazol-4-yl)-2-(1,5-dihydroxy-4-pyridon-2-ylmethoxyimino)acetamido]-3(1-methyl-1H-tetrazol-5-ylthiomethyl)-3-cephem-4carboxylic acid

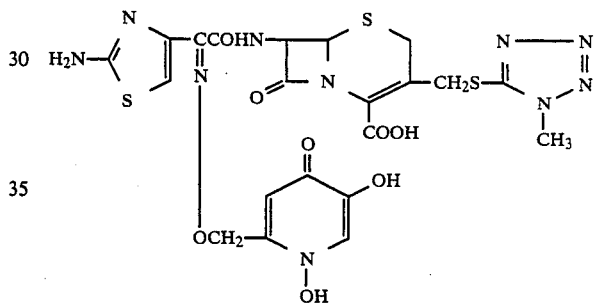

4.465 g (5 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 50 ml of dichloromethane. Then, 0.766 g (5 mmol) of 1-hydroxybenzotriazole and 1.03 g (5 mmol) of dicyclohexylcarbodiimide were added under cooling with ice, and the mixture was stirred for 1 hour on ice bath. Then, 2.473 g (5 mmol) of benzhydryl 7-amino-3-(1-methyl-1H-tetrazol-5-ylthiomethyl)-3-cephem-4-carboxylate was added thereto, and the mixture was stirred at room temperature for 16 hours under stirring. Precipitated insolubles were removed by filtration, and the filtrate was concentrated to dryness and subjected to silica gel column chromatography and eluted with benzene/ethyl acetate (4/1 to ½) to obtain 4.6 g of benzhydryl (6R, 7R)-7-[(Z)-2(2-tritylaminothiazol-4-yl)-2-(1,5-dibenzhydryloxy-4-pyridon-2-ylmethoxyimino)acetamido]-3-(1-methyl-1H-tetrazol-5-ylthiomethyl)-3-cephem-4-carboxylate.

4.1 g of the carboxylate thus prepared was dissolved in a mixture of 2 ml of anisole and 12 ml of trifluoroacetic acid, and the mixture was reacted at room temperature for 2 hours. The reaction solution was poured into 50 ml of diethyl ether, and formed precipitates were collected by filtration to obtain 1.968 g of a trifluoroacetate of the above identified compound.

NMR(DMSO-d$_6$)δ(ppm): 3.69(2H,bs), 3.95(3H,s), 4.35(2H,bs), 5.19(1H,d,J=4Hz), 5.39(2H,s), 5.82(1H,bs), 6.96(1H,s), 7.19(1H,s), 8.25(1H,s), 9.80(1H,d,J=8Hz).

KR(KBr):νc=o 1790 cm⁻¹.

1.268 g of the above trifluoroacetate was suspended in 30 ml of water and adjusted to pH 7 with a sodium hydrogencarbonate solution. The solution thus obtained was washed with ethyl acetate, and the aqueous layer was subjected to HP-20 column chromatography. The fraction eluted with ethanol/water (4/1) was concentrated and freeze-dried to obtain 0.3 g of a sodium salt of the above identified compound.

EXAMPLE 6

(6R, 7R)-7-[(Z)-2-(2-aminothiazol-4-yl)-2-(1,5-dihydroxy-4-pyridon-2-ylmethoxyimino)acetamido]-3-[-(1(2-hydroxyethyl)-1H-tetrazol-5-ylthiomethyl]-3-cephem-4-carboxylic acid

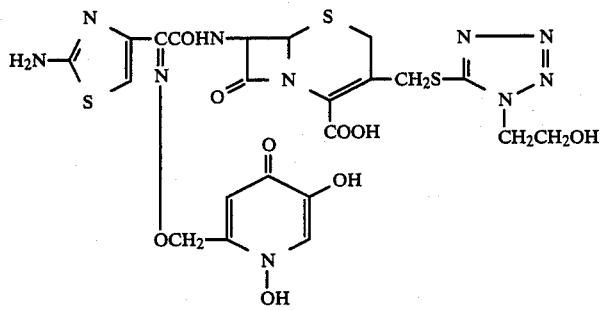

1.242 g (1 mmol) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-chloromethyl-3-cephem-4-carboxylate obtained in Example 2 was dissolved in a solvent mixture of 10 ml of dimethylformamide and 20 ml of ethanol. Then, 0.161 g (1.1 mmol) of 1-(2-hydroxyethyl)-1H-tetrazole-5-thiol in 35 ml of ethanol and 0.21 ml (1.1 mmol) of 5.2N sodium methoxide were added thereto under cooling with ice, and the mixture was reacted for 25 hours under stirring. The reaction solution was poured into ice. Precipitated crystals were collected by filtration and subjected to silica gel column chromatography and eluted with chloroform/methanol (30/1) to obtain 0.97 g of p-methoxybenzyl (6R,7R)-7-[(Z)-2-(2-tritylaminothiazol-4-yl)-2-(1,5-dibenzhydryloxy-4-pyridon-2-ylmethoxyimino)acetamido]-3-[-1-(2-hydroxyethyl)-1H-tetrazol-5-ylthiomethyl]-3-cephem-4-carboxylate.

0.97 g of the carboxylate thus prepared was added to a mixture of 10 ml of trifluoroacetic acid and 1 ml of anisole, and reacted for 1 hour under stirring and cooling with water. The reaction solution was concentrated, and 100 ml of diethyl ether was added thereto. Formed precipitates were collected by filtration to obtain 0.535 g of a trifluoroacetate of the above identified compound.

NMR(DMSO-d₆) δ(ppm):
3.75(4H,bs), 4.35(4H,bs), 6.20(1H,bs), 6.40(2H,bs), 6.80(1H,bs), 7.00(1H,s), 7.15(1H,s), 8.17(1H,s), 9,80(1H,d).

IR(KBr): νc=o 1790 cm⁻¹.

0.535 g of the above trifluoroacetate was suspended in 20 ml of water, and adjusted to pH 7.0 with a 2% sodium hydrogencarbonate solution. The solution thus obtained was subjected to Amberlite XAD-2 column chromatography to obtain 0.4 g of a sodium salt of the above identified compound.

EXAMPLE 7

(6R, 7R)-7-[(Z)-2-(2-aminothiazol-4-yl)-2-(1,5-dihydroxy-4-pyridon-2-ylmethoxyimino)acetamido]-3-(1-carboxymethyl-1H-tetrazol-5-ylthiomethyl)-3-cephem-4-carboxylic acid

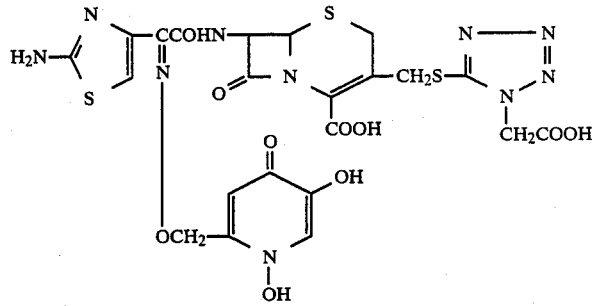

7.145 g (8 mmol) of (Z)-2-(2-tritylaminothiazol-4-yl)-2-(1,5-dibenzhydryloxy-4-pyridon-2-ylmethoxyimino)-acetic acid obtained in Example 1 was dissolved in 130 ml of dichloromethane. Then, 1.225 g (8 mmol) of 1-hydroxybenzotriazole and 1.648 g (8 mmol) of dicyclohexyl carbodiimide were added thereto under cooling with ice, and the mixture was stirred for 1 hour on ice bath. Then, 6.195 g (8.8 mmol) of benzhydryl 7-amino-3-(1-benzhydryloxycarbonylmethyl-1H-tetrazol-5-ylthiomethyl)-3-cephem-4-carboxylate was added thereto, and reacted at room temperature for 16 hours under stirring. Precipitated insolubles were removed by filtration, and the filtrate was concentrated to dryness and subjected to silica gel column chromatography and eluted with chloroform/acetone (50/1 to 10/1) to obtain 11.4 g of benzhydryl (6R, 7R)-7-[(Z)-2-(2-tritylaminothiazol-4-yl)-2-(1,5-dibenzhydryloxy-4-pyridon-2- ylmethoxyimino)acetamido]-3-(1-benzhydryloxycarbonylmethyl-1H-tetrazol-5-ylthiomethyl)-3-cephem-4-carboxylate.

10 g of the carboxylate thus obtained was dissolved in a mixture of 5 ml of anisole and 50 ml of trifluoroacetic acid, and reacted at room temperature for 2 hours. The reaction solution was poured into 400 ml of diethyl ether, and formed precipitates were collected by filtration to obtain 5.0 g of a trifluoroacetate of the above identified compound.

NMR(DMSO-d$_6$) δ(ppm):
3.73(2H,bs), 4.40(2H,bs), 5,32(5H,s), 5.83(1H,bs), 6.97(1H,s), 7.20(1H,s), 8.27(1H,s), 9.85(1H,bs).
IR(KBr) $\nu$c=o: 1780 cm$^{-1}$.

5.0 g of the above trifluoroacetate was suspended in 100 ml of water, and adjusted to pH 7 with a sodium hydrogencarbonate solution. The solution thus obtained was washed with ethyl acetate, and the aqueous phase was subjected to HP-20 column chromatography. The fraction eluted with ethanol/water (4/1) was concentrated and freeze-dried to obtain 0.85 g of a sodium salt of the above identified compound.

EXAMPLE 8

(6R, 7R)-7-[(Z)-2-(2-aminothiazol-4-yl)-2-(1,5-dihydroxy-4-pyridon-2-ylmethoxyimino)acetamido]-3-[1-(2-dimethylaminoethyl)-1H-tetrazol-5-ylthiomethyl]-3-cephem-4-carboxylic acid

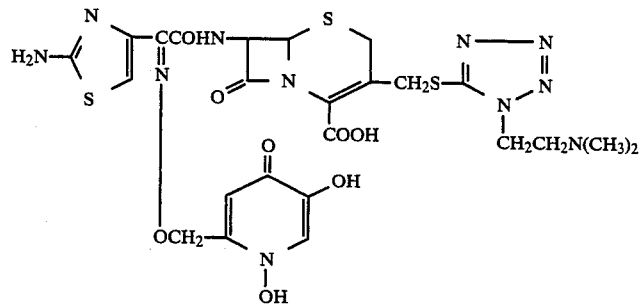

1.242 g (1 mmol) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-chloromethyl-3-cephem-4-carboxylate obtained in Example 2 was dissolved in 10 ml of dimethylformamide. Then, 0.213 g (1.1 mmol) of sodium 1-(2-dimethylaminoethyl)-1H-tetrazole-5-thiolate in dimethylformamide was added thereto under cooling with ice at −20° C., and the mixture was reacted under stirring for 3 hour. The reaction solution was poured to ice. Precipitated crystals were collected by filtration and then subjected to silica gel column chromatography and eluted with chloroform/methanol (10/1) to obtain 0.745 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-[1-(2-dimethylaminoethyl)-1H-tetrazol-5-ylthiomethyl]-3-cephem-4-carboxylate.

0.745 g of the carboxylate thus obtained was dissolved in a mixture of 10 ml of trifluoroacetic acid and 1 ml of anisole, and reacted for 2 hours under stirring. The reaction solution was concentrated, and then 100 ml of diethyl ether was added thereto. Formed precipitates were collected by filtration to obtain 0.490 g of a trifluoroacetate of the above identified compound.

NMR(DMSO-d$_6$) δ(ppm);
2.90(6H,s), 3.70(4H,m), 4.35(2H,bs), 4.55(2H,bs), 5.20(1H,m), 5.40(2H,bs), 5.85(1H,m), 6.85(1H,s), 7.15(1H,s).

0.490 g of the above trifluoroacetate was suspended in 20 ml of water, and adjusted to pH 7.0 with a 2% sodium hydrogencarbonate solution. The solution thus obtained was subjected to Amberlite XAD-2 column chromatography. The fraction eluted with ethanol/water (4/1) was concentrated and freeze-dried to obtain 0.294 g of a sodium salt of the above identified compound.

IR(KBr): $\nu$c=o 1790 cm$^{-1}$.

The sodium salt was dissolved in water and adjusted to pH 1.1 with 1N hydrochloric acid to obtain a hydrochloride of the above identified compound.

EXAMPLE 9

(6R, 7R)-7-[(Z)-2-(2-aminothiazol-4-yl)-2-(1,5-dihydroxy-4-pyridon-2-ylmethoxyimino)acetamido]-3-(1,3,4-thiadiazol-5-ylthiomethyl)-3-cephem-4-carboxylic acid

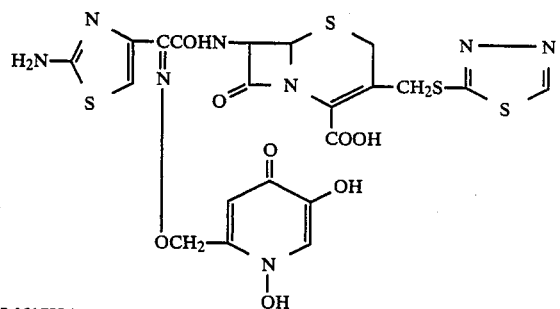

4.465 g (5 mmol) of (Z)-2-(2-tritylaminothiazol-4-yl)-2-(1,5-dibenzhydryloxy-4-pyrion-2-ylmethoxyimino)acetic acid obtained in Example 1 was dissolved in 50 ml of dichloromethane. Then, 0.766 g (5 mmol) of 1-hydroxybenzotriazole and 1.03 g (5 mmol) of dicyclohexylcarbodiimide were added thereto under cooling with ice, and the mixture was stirred for 1 hour on ice bath. Then, 2.7 g (6 mmol) of p-methoxybenzyl 7-amino-3-(1,3,4-thiadiazol-5-ylthiomethyl)-3-cephem-4-carboxylate was added thereto, and reacted at room temperature for 16 hours under stirring. Precipitated insolubles were removed by filtration, and the filtrate was concentrated to dryness and subjected to silica gel, column chromatography and eluted with chloroform/acetone (17/1 to 3/1) to obtain 4.1 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(1,3,4-thiadiazol-5-ylthiomethyl)-3-cephem-4-carboxylate.

2.1 g of the carboxylate thus obtained was dissolved in a mixture of 1 ml of anisole and 6 ml of trifluoroacetic acid, and reacted at room temperature for 2 hours. The reaction solution was poured into 50 ml of diethyl ether. Formed precipitates were collected by filtration to obtain 1.254 g of a trifluoroacetate of the above identified compound.

NMR(DMSO-$d_6$) δ(ppm):
3.80(2H,s), 4,39(2H,bs), 5.18(1H,d,J=4Hz), 5.38(2H,s), 5.85(1H,bs), 6.96(1H,s), 7.21(1H,s), 7.34(1H,s), 8.27(1H,s).
IR(KBr): $\nu c=o$ 1780 cm$^{-1}$.

1.0 g of the above trifluoroacetate was suspended in 50 ml of water, and adjusted to pH 7 with a sodium hydrogencarbonate solution. The solution thus obtained was washed with ethyl acetate, and the aqueous layer was subjected to HP-20 column chromatography. The fraction eluted with ethanol/water (4/1) was concentrated and freeze-dried to obtain 0.55 g of a sodium salt of the above identified compound.

EXAMPLE 10

(6R, 7R)-7-[(Z)-2-(2-aminothiazol-4-yl)-2-(1,5-dihydroxy-4-pyridon-2-ylmethoxyamino)acetamido]-3-(2-methyl-1,3,4-thiadiazol-5-ylthiomethyl)-3-cephem-4-carboxylic acid

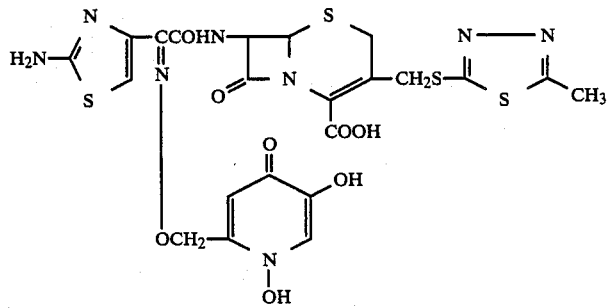

3.57 g (4 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 80 ml of dichloromethane. Then, 0.613 g (4 mmol) of 1-hydroxybenzotriazole and 0.824 g (4 mmol) of dicyclohexylcarbodiimide were added thereto under cooling with ice, and the mixture was stirred for 1 hour on ice bath. Then, 1.86 g (4 mmol) of p-methoxybenzyl 7-amino-3-(2-methyl-1,3,4-thiadiazol-5-ylthiomethyl)-3-cephem-4-carboxylate was added thereto, and reacted at room temperature for 18 hours under stirring. Precipitated insolubles were removed by filtration, and the filtrate was concentrated to dryness, and subjected to silica gel column chromatography and eluted with chloroform/ethyl acetate (½) to obtain 1.3 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(2-methyl-1,3,4-thiadiazol-5-ylthiomethyl)-3-cephem-4-carboxylate. 1.0 g of the carboxylate thus prepared was dissolved in a mixture of 1 ml of anisole and 3.3 ml of trifluoroacetic acid, and reacted at room temperature for 3 hours. The reaction solution was poured into 30 ml of diethyl ether, and formed precipitates were collected by filtration to obtain 0.6 g of a trifluoroacetate of the above identified compound.

NMR(DMSO-$d_6$) δ(ppm):
2.67(3H,s), 3.73(2H,s), 4.20(2H,bs), 5.14(1H,bs), 5.36(2H,s), 5.80(1H,bs), 6.90(1H,s), 7.24(1H,s), 8.20(1H,s).
IR(KBr): $\nu c=o$ 1770 cm$^{-1}$.

0.6 g of the above trifluoroacetate was suspended in 10 ml of water, and adjusted to pH 7 with a sodium hydrogencarbonate solution. The solution thus obtained was washed with ethyl acetate, and the aqueous phase was subjected to XAD-2 column chromatography. The fraction eluted with methanol/water (4/1) was concentrated and freeze-dried to obtain 0.314 g of a sodium salt of the above identified compound.

EXAMPLE 11

(6R, 7R)-7-[(Z)-2-(2-aminothiazol-4-yl)-2-(1,5-dihydroxy-4-pyridon-2-ylmethoxyimino)acetamido]-3-(1,2,3-triazol-5-ylthiomethyl)-3-cephem-4-carboxylic acid

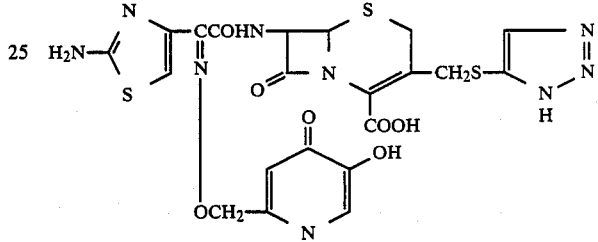

5.4 g (6 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 100 ml of dichloromethane. Then, 0.918 g (6 mmol) of 1-hydroxybenzotriazole and 1.24 g (6 mmol) of dicyclohexyl carbodiimide were added thereto under cooling with ice, and the mixture was stirred for 1 hour on ice bath. Then, 3.5 g (6.7 mmol) of p-methoxybenzyl 7-amino-3-(1-tetrahydropyranyl-1,2,3-triazol-5-ylthiomethyl)-3-cephem-4-carboxylate was added thereto, and reacted at room temperature for 18 hours under stirring. Precipitated insolubles were removed by filtration, and the filtrate was concentrated by dryness and subjected to silica gel column chromatography and eluted with chloroform/acetone (2/1) to obtain 4.6 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(1-tetrahydropyranyl-1,2,3-triazol-5-ylthiomethyl)-3-cephem-4-carboxylate.

1.0 g of the carboxylate thus obtained was dissolved in a mixture of 1 ml of anisole and 3.3 ml of trifluoroacetic acid, and reacted at room temperature for hours. The reaction solution was poured into 30 ml of diethyl ether, and formed precipitates were collected by filtration to obtain 0.48 g of a trifluoroacetate of the above identified compound.

NMR(DMSO-$d_6$) δ(ppm)
3.70(2H,bs), 4.00(2H,bs), 5.12(1H,bs), 5.20(2H,s), 5.73(1H,bs), 6.82(1H,s), 6.88(1H,s), 7.27(1H,s), 7.90(1H,s).
KR(KBr: $\nu c=o$ 1775 cm$^{-1}$.

0.48 g of the above trifluoroacetate was suspended in 50 ml of water, and adjusted to pH 7 with a sodium hydrogencarbonate solution. The solution thus obtained was washed with ethyl acetate, and the aqueous phase was subjected to XAD-2 column chromatography. The fraction eluted with methanol/water (4/1) was concentrated and freeze-dried to obtain 0.15 g of a sodium salt of the above identified compound.

EXAMPLE 12

(6R, 7R)-7-[(Z)-2-(2-aminothiazol-4-yl)-2-(1,5-dihydroxy-4-pyridon-2-ylmethoxyimino)acetamido]-3-(2,5-dihydro-6-hydroxy-2-methyl-5-oxo-as-triazin-3-ylthiomethyl)-3-cephem-4-carboxylic acid

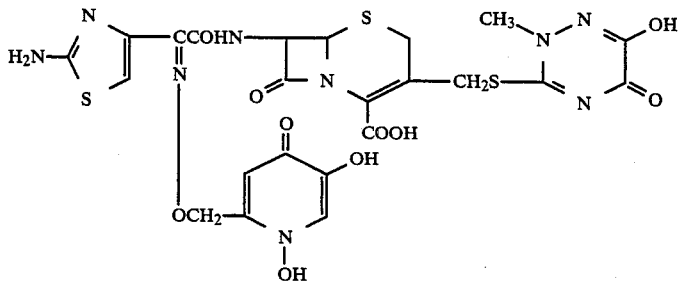

7.415 g (8 mmol) of (Z)-2-(2-tritylaminothiazol-4-yl)-2-(1,5-dibenzhydryloxy-4-pyridon-2-ylmethoxyimino)-acetic acid obtained in Example 1 was dissolved in 50 ml of dichloromethane. Then, 1.225 g (8 mmol) of 1-hydroxybenzotriazole and 1.648 g (8 mmol) of dicyclohexylcarbodiimide were added thereto under cooling with ice, and the mixture was stirred for 1 hour on ice bath. Then, 6.186 g (8.8 mmol) of benzhydryl 7-amino-3-(2,5-dihydro-6-benzhydryloxy-2-methyl-5-oxo-astriazin-3-ylthiomethyl)-3-cephem-4-carboxylate was added thereto, and reacted at room temperature for 16 hours under stirring. Precipitated insolubles were removed by filtration, and the filtrate was concentrated to dryness, and subjected to silica gel column chromatography and eluted with chloroform/acetone (50/1 to 10/1) to obtain 11 g of benzhydryl (6R, 7R)-7-[(Z)-2-(2-tritylaminothiazol-4-yl)-2-(1,5-dibenzhydryloxy-4-pyridon-2-ylmethoxyimino)-acetamido]-3-(2,5-dihydro-6-benzhydryloxy-2-methyl-5-oxo-as-triazin-3-ylthiomethyl)-3-cephem-4-carboxylate.

11 g of the carboxylate thus obtained was dissolved in a mixture of 5 ml of anisole and 50 ml of trifluoroacetic acid, and the mixture was reacted at room temperature for 2 hours. The reaction solution was poured into 400 ml of diethyl ether. Formed precipitates were collected by filtration to obtain 7.0 g of a trifluoroacetate of the above identified compound.

NMR(DMSO-$d_6$) δ(ppm):
3.67(2H,s), 3.76(3H,s), 4.24(2H,bs), 5.23-5.94(4H,bs), 7.04(1H,s), 7.28(1H,s), 8.32(1H,s), 9.93(1Hbs).
IR(KBr): $\nu c=o$ 1780 cm$^{-1}$.

4.572 g of the above trifluoroacetate was suspended in 100 ml of water, and adjusted to pH 7 with a sodium hydrogencarbonate solution. The solution thus obtained was washed with ethyl acetate, and the aqueous phase was subjected to HP-20 column chromatography. The fraction eluted with ethanol/water (4/1) was concentrated and freeze-dried to obtain 1.89 g of a sodium salt of the above identified compound.

EXAMPLE 13

(6R, 7R)-7-[(Z)-2-(2-aminothiazol-4-yl)-2-(1,5-dihydroxy-4-pyridon-2-ylmethoxyimino)acetamido]-3-(5-ethoxycarbonylmethyl-4-methylthiazol-2-ylthiomethyl)-3-cephem-4-carboxylic acid

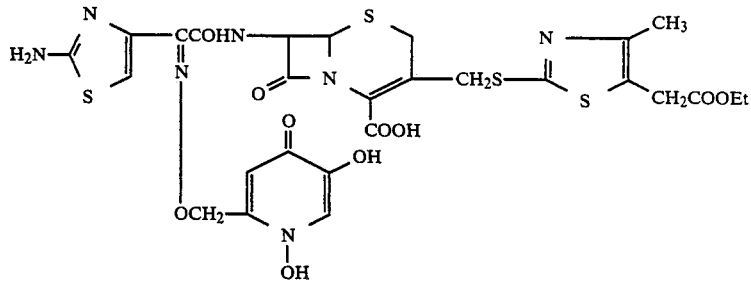

4.465 g (5 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 50 ml of dichloromethane. Then, 0.766 g (5 mmol) of 1-hydroxybenzotriazole and 1.03 g (5 mmol) of dicyclohexyl carbodiimide were added thereto under cooling with ice, and the mixture was stirred for 1 hour on ice bath. Then, 4.146 g (6 mmol) of p-methoxybenzyl 7-amino-3-(5-ethoxycarbonylmethyl-4-methylthiazol-2- ylthiomethyl)-3-cephem-4-carboxylate was added, and reacted at room temperature for 16 hour under stirring. Precipitated insolubles were removed by filtration, and the filtrate was concentrated to dryness, and subjected to silica gel column chromatography and eluted with chloroform/ethyl acetate (9/1 to ½) to obtain 5.0 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(5-ethoxycarbonylmethyl-4-methylthiazol-2-ylthiomethyl)-3-cephem-4-carboxylate.

0.5 g of the carboxylate thus obtained was dissolved in a mixture of 2 ml of anisole and 12 ml of trifluoroacetic acid, and the mixture was reacted at room temperature for 2 hours. The reaction solution was poured into 160 ml of diethyl ether, and formed precipitates were collected by filtration to obtain 2.798 g of a trifluoroacetate of the above identified compound.

NMR(DMSO-d$_6$) δ(ppm): 1.20(3H,t,J=7Hz), 2.26(3H,s), 3.72(2H,bs), 3.82(2H,s), 3.86-4.35(4H,m), 5.15(1H,d,J=4Hz), 5.38(2H,s), 6.17(1H,bs), 6.91(1H,s), 7.16(1H,s), 8.23(1H,s), 9.80(1H,d,J=7Hz).

IR(KBr): $\nu$c=o 1790 cm$^{-1}$.

2.5 g of the above-mentioned trifluoroacetate was suspended in 100 ml of water, and adjusted to pH 7 with a sodium hydrogencarbonate solution. The solution thus obtained was washed with ethyl acetate, and the aqueous phase was subjected to HP-20 column chromatography. The fraction eluted with ethanol/water (4/1) was concentrated and freeze-dried to obtain 1.3 g of a sodium salt of the above identified compound.

EXAMPLE 14

(6R, 7R)-7-[(Z)-2-(2-aminothiazol-4-yl)-2-(1,5-dihydroxy-4-pyridon-2-ylmethoxyimino)acetamido]-3-(4-carboxy-3-hydroxyisothiazol-5-ylthiomethyl)-3-cephem-4-carboxylic acid

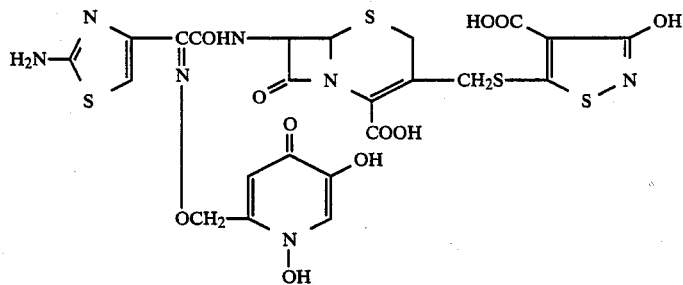

150 mg (0.116 mmol) of benzhydryl (6R, 7R)-7-[(Z)-2-(2-tritylaminothiazol-4-yl)-2-(1,5-dibenzhydryloxy-4-pyridon-2-ylmethoxyimino)acetamido]-3-chloromethyl-3-cephem-4-carboxylate obtained in Example 2 was added to a solvent mixture of 4.5 ml of dimethylformamide, 0.5 ml of methanol and 0.2 ml of water. Then, 30 mg (0.123 mmol) of trisodium 4-carboxy-3-hydroxy-5-mercaptoisothiazole was added thereto, and reacted at room temperature for 18 hours. The reaction solution was added to a solvent mixture of 30 ml of dichloromethane and 20 ml of dilute hydrochloric acid, and the dichloromethane layer was washed with water and dried over anhydrous magnesium sulfate. The solvent was distilled off under reduced pressure, and ethyl ether was added to the residue, followed by conversion into powder to obtain 85 g of benzhydryl (6R, 7R)-7-[(Z)-2--(2-tritylaminothiazol-4-yl)-2-(1,5-dibenzhydryloxy-4-pyridon-2-ylmethoxyimino)-acetamido]-3-(4-carboxy-3-hydroxyisothiazol-5-ylthiomethyl)-3-cephem-4-carboxylate.

80 mg of the carboxylate thus obtained was added to a mixture of 0.07 ml of anisole and 0.9 ml of trifluoroacetic acid, and the mixture was reacted at room temperature for 3 hours under stirring. The solvent was distilled off under reduced pressure, and ethyl ether was added to the residue. Formed precipitates were collected by filtration to obtain 40 mg of a trifluoroacetate of the above identified compound.

NMR(DMSO-d$_6$) δ(ppm):
3.47(2H,bs), 3.67(2H,s), 5.36(3H,bs), 5.90(1H,m) 6.94(1H,s), 7.16(1H,s), 8.25(1H,s).

IR(KBr): $\nu$c=o 1770 cm$^{-1}$.

40 mg of the above trifluoroacetate was added to 10 ml of water, and adjusted to pH 7.0 with a 2% sodium hydrogencarbonate solution. The solution thus obtained was subjected to XAD-2 column chromatography. The fraction eluted with ethanol/water (4/1) was concentrated and freeze-dried to obtain 30 mg of a sodium salt of the above identified compound.

EXAMPLE 15

(6R, 7R)-7-[(Z)-2-(2-aminothiazol-4-yl)-2-(1,5-dihydroxy-4-pyridon-2-ylmethoxyimino)acetamido]-3-acetoxymethyl-3-cephem-4-carboxylic acid

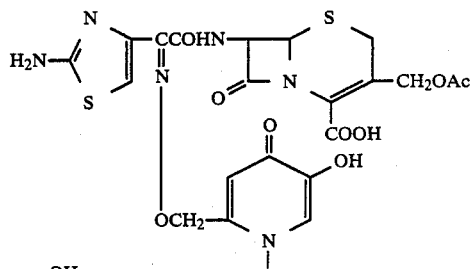

1.786 g (2 mmol) of (Z)-2-(2-tritylaminothiazol-4-yl)-2-(1,5-dibenzhydryloxy-4-pyridon-2-ylmethoxyimino)acetic acid obtained in Example 1 was dissolved in 20 ml of dichloromethane. Then, 0.308 g (2 mmol) of 1-hydroxy-benzotriazole and 0.412 g (2 mmol) of dicyclohexyl carbodiimide were added thereto under cooling with ice, and the mixture was stirred for 1 hour on ice bath. Then, 0.691 g (2 mmol) of t-butyl 7-amino-3-acetoxymethyl-3-cephem-4-carboxylate was added thereto, and reacted at room temperature for 16 hours under stirring. Precipitated insolubles were removed by filtration, and the filtrate was concentrated to dryness and subjected to silica gel column chromatography and eluted with benzene/ethyl acetate (2/1 to ½) to obtain 1.1 g of t-butyl (6R, 7R)-7-[(Z)-2-(2-tritylaminothiazol-4-yl)-2-(1,5-dibenzhydryloxy-4-pyridon-2-ylmethoxyimino)acetamido]-3-acetoxymethyl-3-cephem-4-carboxylate.

1.1 g of the carboxylate thus prepared was dissolved in a mixture of 2 ml of anisole and 8 ml of trifluoroacetic acid, and the mixture was reacted at room temperature for 2 hours. The reaction solution was poured into 50 ml of diethyl ether, and formed precipitates were collected by filtration to obtain 0.577 g of a trifluoroacetate of the above identified compound.

NMR(DMSO-d$_6$) δ(ppm):
2.07(3H,s), 3.58(2H,s), 5.25(1H,d,J=4Hz),
5.45(2H,s), 5.92(1H,bs), 7.03(1H,s),7.27(1H,s) 8.14(1H,s), 9.88(1H,bs).

IR(KBr): νc=o 1780 cm$^{-1}$.

0 5 g of the above trifluoroacetate was suspended in 10 ml of water and adjusted to pH 7 with a sodium hydrogencarbonate solution. The solution thus obtained was washed with ethyl acetae, and the aqueous phase was subjected to HP-20 column chromatography. The fraction eluted with ethanol/water (4/1) was concentrated and freeze-dried to obtain 0.25 g of a sodium salt of the above identified compound.

EXAMPLE 16

(6R, 7R)-7-[(Z)-2-(2-aminothiazol-4-yl)-2-(1,5-dihydroxy-4-pyridon-2-ylmethoxyimino)acetamido]-3-vinyl-3-cephem-4-carboxylic acid

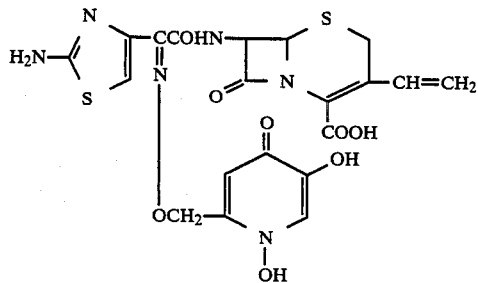

1.85 g (2 mmol) of (Z)-2-(2-tritylaminothiazol-4-yl)-2-(1,5-dibenzhydryloxy-4-pyridon-2-ylmethoxyimino)-acetic acid obtained in Example 1 was dissolved in 20 ml of dimethylacetamido. Then, 0.315 g (2 mmol) of 1-hydroxybenzotriazole and 0.423 g (2 mmol) of dicyclohexylcarbodiimide were added thereto under cooling with ice, and the mixture was stirred for 1 hour on ice bath. Then, 5 ml of a dimethylacetamide solution of 0.8 g (2.33 mmol) of p-methoxybenzyl 7-amino-3-vinyl-3-cephem-4-carboxylate was added thereto, and reacted at room temperature for 18 hours under stirring. Precipitated insolubles were removed by filtration, and the filtrate was concentrated to dryness, and subjected to silica gel column chromatography and eluted with benzene/ethyl acetate (⅓) to obtain 1.3 g of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-vinyl-3-cephem-4-carboxylate.

1.2 g of the carboxylate thus prepared was dissolved in a mixture of 1.3 ml of anisole and 4.4 ml of trifluoroacetic acid, and the mixture was reacted at room temperature for 3 hours. The reaction solution was poured into 30 ml of diethyl ether, and formed precipitates were collected by filtration to obtain a trifluoroacetic acid of the above identified compound.

NMR(CD$_3$COCD$_3$) δ(ppm):
3.72(2H,bs), 5.28(1H,d), 5.45(2H,s), 5.93(1H,bs) 7.05(1H,s), 7.22(1H,s), 8.22(1H,s).

IR(KBr): νc=o 1770 cm$^{-1}$.

0.6 g of the above trifluoroacetate was suspended in 30 ml of water, and adjusted to pH 7 with sodium hydrogencarbonate solution. This solution was washed with ethyl acetate, and the aqueous layer was subjected to Amberlite XAD-2 column chromatography. The fraction eluted with methanol/water (4/1) was concentrated and freeze-dried to obtain 0.2 g of a sodium salt of the above identified compound.

EXAMPLE 17

(6R, 7R)-7-[(Z)-2-(2-aminothiazol-4-yl)-2-(1,5-dihydroxy-4-pyridon-2-ylmethoxyimino)acetamido]-3-(5-methyl-2H-tetrazol-2-ylmethyl)-3-cephem-4-carboxylic acid

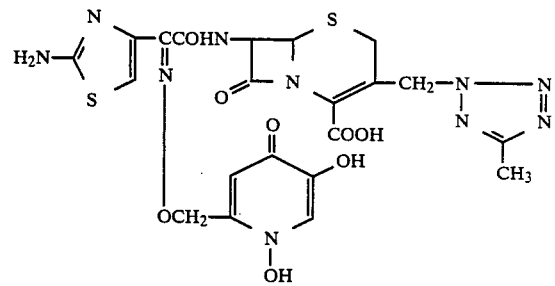

6.31 g (7 mmol) of (Z)-2-(2-tritylaminothiazol-4-yl)-2-(1,5-dibenzhydryloxy-4-pyridon-2-ylmethoxyimino)acetic acid was dissolved in 70 ml of tetrahydrofuran. Then, 1.07 g (7 mmol) of 1-hydroxybenzotriazole and 1.59 g (7.7 mmol) of dicyclohexyl carbodiimide were added thereto under cooling with ice, and the mixture was stirred for 1 hour in ice bath. Then, a solution obtained by dissolving 3.24 g (7 mmol) of p-methoxybenzyl 7-amino-3-(5-methyl-2H-tetrazol-2-ylmethyl)-3-cephem-4-carboxylate in 70 ml of tetrahydrofuran, was added thereto, and the mixture was reacted at room temperature for 16 hours under stirring. Precipitated insolubles were removed by filtration, and the filtrate was concentrated to dryness and subjected to silica gel column chromatography and eluted with chloroform/acetone (100/1 to 10/1) to obtain 6.32 g of p-methoxybenzyl (6R, 7R)-7-[(Z)-2-(2-tritylaminothiazol-4-yl)-2-(1,5-benzhydryloxy-4-pyridon-2-ylmethoxyimino)-acetamido]-3-(5-methyl-2H-tetrazol-2-ylmethyl)-3-cephem-4-carboxylate.

6.01 g of the carboxylate thus obtained was dissolved in a mixture of 6 ml of anisole and 30 ml of trifluoroacetic acid, and the mixture was reacted at room temperature for 1.5 hours. The reaction solution was poured into 200 ml of diisopropyl ether, and formed precipitates were collected by filtration to obtain 3.57 g of a trifluoroacetate of the above identified compound.

NMR(DMSO-d$_6$) δ(ppm):
2.48(3H,s), 3.45(2H,bs), 5.23(1H,d,J=4Hz),
5.38(2H,bs), 5.70(2H,bs), 5.92(1H,dd,J=4.8Hz), 6.97(1H,s), 7.18(1H,s), 8.28(1H,s).

IR(KBr): νc=o 1790 cm$^{-1}$.

3.5 g of the above trifluoroacetate was suspended in 30 ml of water, and 960 mg of sodium hydrogencarbonate was added to obtain a uniform solution. The solution thus obtained was washed with ethyl acetate, and the aqueous phase was subjected to HP-20 column chromatography. The fraction eluted with ethanol/water (4/1) was concentrated and freeze-dried to obtain 2.1 g of a sodium salt of the above identified compound.

EXAMPLE 18

(6R, 7R)-7-[(Z)-2-(2-aminothiazol-4-yl)-2-(1,5-dihydroxy-4-pyridon-2-ylmethoxyimino)acetamido]-3-(1-methyl-pyridinium-4-ylthiomethyl)-3-cephem-4-carboxylate

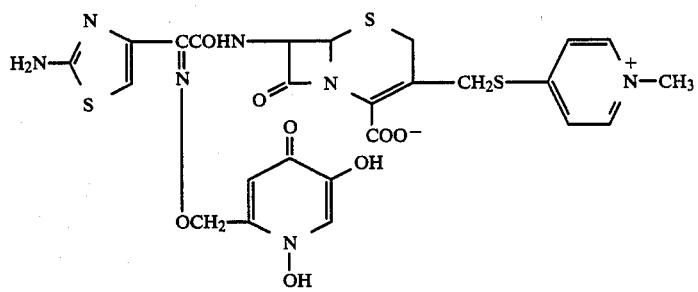

4.3 g (3.43 mmol) of the product of Example 2 was dissolved in dry tetrahydrofuran (200 ml), and 1.17 g (10.3 mmol) of 1-methylpyridine-4-thione was added thereto. The mixture was reacted for 18 hours under stirring and cooling with ice, the reaction solution was concentrated under reduced pressure, and then subjected to silica gel column chromatography and eluted with chloroform/methanol (10/1) to obtain 2.8 g (yield: 59.7%) of p-methoxybenzyl (6R,7R)-7-[(Z)-2-(2-tritylaminothiazol-4-yl)-2-(1,5-dibenzhydryloxy-4-pyridon-2-ylmethoxyimino)acetamido]-3-(1-methyl-pyridinium-4-ylthiomethyl)-3-cephem-4-carboxylate chloride. This product was dissolved in a mixture of trifluoroacetic acid (14 ml) and anisole (2.8 ml). The mixture was reacted for 1 hour under stirring and cooling with ice. Ethyl ether (140 ml) was added to the reaction solution, and formed precipitates were collected by filtration to obtain a trifluoroacetate of the above identified compound.

NMR(DMSO-d$_6$) δ(ppm):
3.68(2H,bs), 4.20(3H,s), 4.40(2H,bs), 5.36(2H,s),
6.89(1H,s), 7.16(1H,s), 7.97(2H,d,J=6.4Hz),
8.21(1H,s), 8.67(2H,d,J=6.4Hz).

IR(KBr): νc=o 1780 cm$^{-1}$.

The above trifluoroacetate was suspended in water (40 ml), and adjusted to pH 7.0 with a 2% sodium hydrogencarbonate solution. Then, it was subjected to HP-20 column chromatography to obtain 0.86 g (yield: 66.7%) of the above identified compound.

EXAMPLE 19

(6R, 7R)-7-[(Z)-2-(2-aminothiazol-4-yl)-2-(1,5-dihydroxy-4-pyridon-2-ylmethoxyimino)acetamido]-3-(2,3-cyclopenteno-1-methylpyridinium-4-ylthiomethy)-3-cephem-4-carboxylate

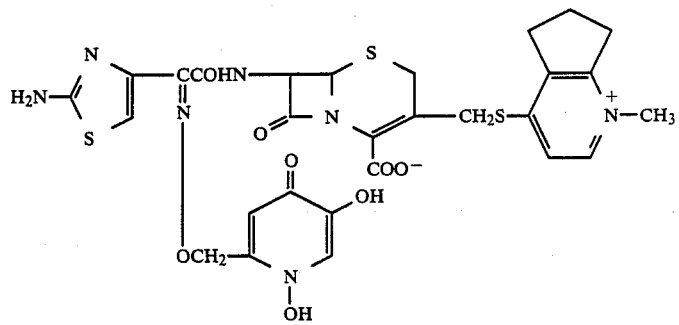

2.6 g (2.1 mmol) of the product of Example 2 was dissolved in dimethylformamide (40 ml), and 1.03 g (6.3 mmol) of 1-methylcyclopenteno[b]pyridine-4-thione was added thereto. The mixture was reacted at room temperature for 3 days under stirring. Chloroform (400 ml) was added to the reaction solution, and washed sequentially with 0.1N hydrochloric acid and a saturated sodium chloride aqueous solution, then dried over anhydrous magnesium sulfate and concentrated to dryness. The residue was subjected to silica gel column chromatography and eluted with chloroform/methanol (10/1) to obtain 1.63 g (yield: 55.4%) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(2,3-cyclopenteno-1-methyl-pyridinium-4-ylthiomethyl)-3-cephem-4-carboxylate chloride. This was dissolved in a mixture of trifluoroacetic acid (8 ml) and anisole (1.6 ml), and the mixture was reacted for 1 hour under stirring and cooling with ice. Ethyl ether (80 ml) was added to the reaction solution, and formed precipitates were collected by filtration to obtain a trifluoroacetate of the above identified compound.

NMR(DMSO-d$_6$) δ(ppm):
1.85-2.51(2H,m), 2.68-3.52(4H,m), 3.70(2H,bs),
4.11(3H,s), 4.46(2H,bs), 5.38(2H,s), 6.95(1H,s),
7.29(1H,s), 7.86(1H,d,J=7Hz), 8.38(1H,s),
8.65(1H,d,J=7Hz).

IR(KBr): νc=o 1768 cm$^{-1}$.

The above trifluoroacetate was suspended in water (20 ml), and adjusted to pH 7.0 with a 2% sodium hydrogencarbonate solution. Then, it was subjected to HP-20 column chromatography to obtain 0.36 g (yield: 45.6%) of the above identified compound.

EXAMPLE 20

Sodium (6R, 7R)-7-[(Z)-2-(2-aminothiazol-4-yl)-2-1,5-dihydroxy-4-pyridon-2-ylmethoxyimino)acetamido]-3-(1-carboxymethylpyridinium-4-ylthiomethyl)-3-cephem-4-carboxylate HP-20 column chromatography to obtain 0.321 g (yield: 40.4%) of the above identified compound.

EXAMPLE 21

Sodium (6R, 7R)-7-[(Z)-2-(2-aminothiazol-4-yl)-2-1,5-dihydroxy-4-pyridon-2-ylmethoxyimino)acetamido]-3-(1-carboxymethyl-2,3-cyclopentenopyridinium-4-ylthiomethyl)-3-cephem-4-carboxylate

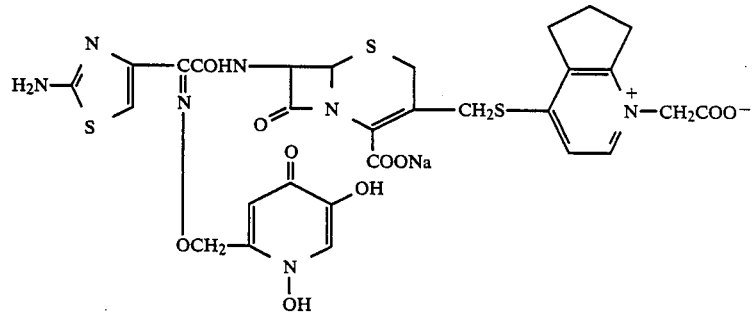

2.6 g (2.1 mmol) of the product of Example 2 was dissolved in dry tetrahydrofuran (50 ml), and 1.67 g (6.3 mmol) of 1-t-butoxycarbonylmethyl-cyclopenteno[b-

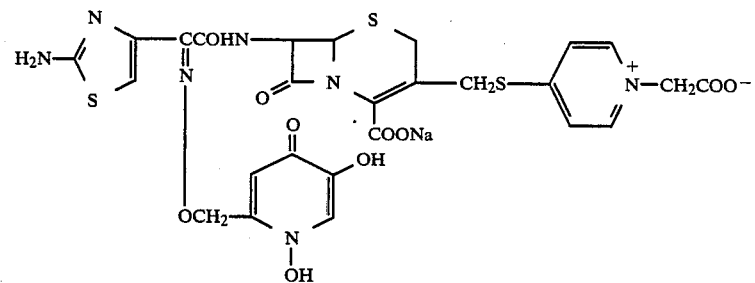

2.6 g (2.1 mmol) of the product of Example 2 was dissolved in dry tetrahydrofuran (50 ml). Then, 1.42 g (6.3 mmol) of 1-t-butoxycarbonylmethylpyridine-4-thione was added thereto, and the mixture was reacted at room temperature for 2 days under stirring. The reaction solution was concentrated under reduced pressure and then subjected to silica gel column chromatography and eluted with chloroform/methanol (10/1) to obtain 1.65 g (yield: 53.7%) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(1-t-butoxycarbonylmethylpyridinium-4-ylthiomethyl)-3-cephem-4-carboxylate chloride.

This product was dissolved in a mixture of trifluoroacetic acid (17 ml) and anisole (3.4 ml), and reacted at room temperature for 4 hours under stirring. Ethyl ether (200 ml) was added to the reaction solution, and formed precipitates were collected by filtration to obtain a trifluoroacetate of the above identified compound.

NMR(DMSO-$d^6$) δ(ppm):
3.68(2H,bs), 4.40(2H,bs), 5.36(2H,s), 5.37(2H,s), 6.90(1H,s), 7.13(1H,s), 8.06(2H,d,J=7Hz), 8.23(1H,s), 8.76(2H,d,J=7Hz).

IR(KBr): νc=o 1780 cm$^{-1}$.

The above trifluoroacetate was suspended in water (80 ml), and adjusted to pH 7.0 with a 2% sodium hydrogencarbonate solution. Then, it was subjected to ]pyridine- 4-thione. The mixture was reacted at room temperature for 2 days under stirring. The reaction solution was concentrated under reduced pressure, and subjected to silica gel column chromatography and eluted with chloroform/methanol (10/1) to obtain 1.8 g (56.4%) of p-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(1-t-butoxycarbonylmethyl-2,3-cyclopentenopyridinium-4-ylthiomethyl)-3-cephem-4-carboxylate chloride. This product was dissolved in a mixture of trifluoroacetic acid (18 ml) and anisole (3.6 ml). Ethyl ether (240 ml) was added to the reaction solution, and formed precipitates were collected by filtration to obtain a trifluoroacetate of the above identified compound.

NMR(DMSO-$d_6$) δ(ppm):
2.20–2.53(2H,m), 2.70-3.40(4H,m), 3.70(2H,bs), 4.44(2H,bs), 5.33(2H,bs), 5.36(2H,s), 6.93(1H,s), 7.14(1H,s), 7.92(1H,d,J=8Hz), 8.23(1H,s), 8.64(1H,d,J=8Hz).

IR(KBr): νc=o 1783 cm$^{-1}$.

The above trifluoroacetate was suspended in water (80 ml), and adjusted to pH 7.0 with a 2% sodium hydrogencarbonate solution. It was then subjected to HP-20 column chromatography, to obtain 0.517 g (yield: 58.0%) of the above identified compound.

EXAMPLE 22

(6R, 7R)-7-[(Z)-2-(2-aminothiazol-4-yl)-2-(1,5-dihydroxy-4-pyridon-2-ylmethoxyimino)acetamido]-3-(1-t-butoxycarbonylmethylpyridinium-4-ylthiomethyl)-3-cephem-4-carboxylate

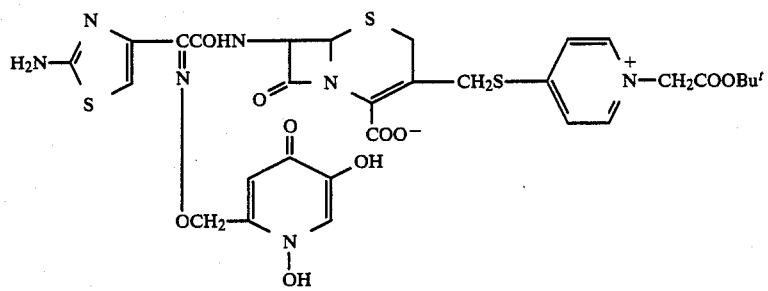

1.65 g (1.12 mmol) of the reaction intermediate of Example 20 t-methoxybenzyl (6R, 7R)-7-[(Z)-2-(2-tritylaminothiazol-4-yl)-2-(1,5-dibenzhydryloxy-4-pyridon-2-ylmethoxyimino)acetamido]-3-(1-t-butoxycarbonylmethylpyridinium-4-ylthiomethyl)-3-cephem-4-carboxylate chloride was dissolved in a mixture of trifluoroacetic acid (8.5 ml) and anisole (1.7 mmol), and reacted for 1 hour under stirring and cooling with ice. Ethyl ether (100 ml) was added to the reaction solution, and formed precipitates were collected by filtration to obtain a trifluoroacetate of the above identified compound.

IR(KBr): $\nu c{=}o$ 1784 cm$^{-1}$.

The above trifluoroacetate was suspended in water (80 ml) and adjusted to pH 7.0 with a 2% sodium hydrogencarbonate solution. Then, it was subjected to HP-20 column chromatography to obtain 0.325 g (yield: 38.9%) of the above identified compound.

EXAMPLE 23

(6R, 7R)-7-[(Z)-2-(2-aminothiazol-4-yl)-2-(1,5-dihydroxy-4-pyridon-2-ylmethoxyimino)acetamido]-3-(1-t-butoxycarbonylmethyl-2,3-cyclopentenopyridinium-4-ylthiomethyl)-3-cephem-4-carboxylate

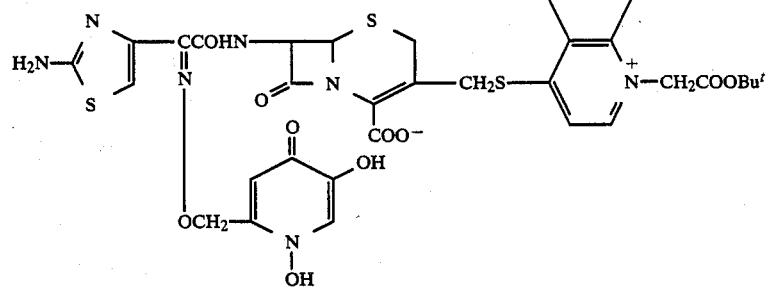

1.8 g (1.19 mmol) of the reaction intermediate of Example 21 p-methoxybenzyl (6R, 7R)-7-[(Z)-2-(2-tritylaminothiazol-4-yl)-2-(1,5-dibenzhydryloxy-4-pypridon-2-ylmethoxyimino)acetamido]-3-(1-t-butoxycarbonylmethyl-2,3-cyclopentenopyridinium-4-ylthiomethyl)-3-cephem-4-carboxylate chloride was dissolved in a mixture of trifluoroacetic acid (9 ml) and anisole (1.8 ml), and reacted for 1 hour under stirring and cooling with ice. Ethyl ether (100 ml) was added to the reaction solution, and formed precipitates were collected by filtration to obtain a trifluoroacetate of the above identified compound.

NMR(DMSO-d$_6$) δ(ppm):
1.48(9H,s), 1.99–2.55(2H,m), 2.72-3.52(4H,m),
3.69(2H,bs), 4.43(2H,bs), 5.37(2H,s), 5.40(2H,s),
6.90(1H,s), 7.19(1H,s), 7.91(1H,d,J=8Hz),
8.28(1H,s), 8.65(1H,d,J=8Hz).

IR(KBr): $\nu c{=}o$ 1782 cm$^{-1}$.

The above trifluoroacetate was suspended in water (80 ml), and adjusted to pH 7.0 with a 2% sodium hydrogencarbonate solution. Then, it was subjected to HP-20 column chromatography to obtain 0.55 g (yield: 8.8%) of the above identified compound.

EXAMPLE 24

(6R, 7R)-7-[(Z)-2-(2-aminothiazol-4-yl)-2-(1,5-dihydroxy-4-pyridon-2-ylmethoxyimino)acetamido]-3-(5-methyl-s-triazolo[1,5-a]pyrimidin-7-ylthiomethyl)-3-cephem-4-carboxylic acid

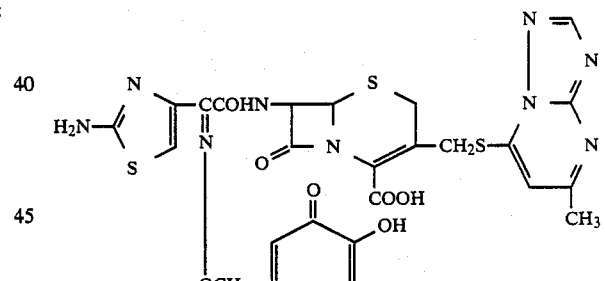

3.8 g (5 mmol) of (Z)-2-(2-tritylaminothiazol-4-yl)-2-(1,5-dibenzhydryloxy-4-pyridon-2-ylmethoxyimino)a- cetic acid obtained in Example 1 was dissolved in 20 ml of tetrahydrofuran. Then, 765 mg (5 mmol) of 1-hydroxybenzotriazole and 1.03 g (5.5 mmol) of cyclohexylcarbodiimide were added thereto under cooling with ice, and the mixture was stirred for 2 hours on water bath. Then, 2.5 g (5 mmol) of p-methoxybenzyl 7-amino-3-(5-methyl-s-triazolo[1,5-a]pyrimidin-7-yl-thiomethyl)-3-cephem-4-carboxylate was added thereto, and reacted at room temperature for 16 hours under stirring. Precipitated insolubles were removed by filtration, and the filtrate was dried under reduced pressure, and then subjected to silica gel column chromatography and eluted with ether/tetrahydrofuran (2/1 to 1/2) to obtain 3.0 g of p-methoxybenzyl (6R, 7R)-7-[(Z)-2-tritylaminothiazol-4-yl)-2-(1,5-dibenzhydryloxy-4-pyridon-2-ylmethoxyimino)-acetamido]-3-(5-methyl-s-triazolo[1,5-a]pyrimidin-7-ylthiomethyl)-3-cephem-4-carboxylate.

This carboxylate was added to a mixture of 15 ml of trifluoroacetic acid and 3 ml of anisole, and the mixture was stirred at room temperature for 2 hours. The reaction solution was poured into 200 ml of isopropyl ether, and formed precipitates were collected by filtration to obtain 2.0 g of a trifluoroacetate of the above identified compound.

NMR(DMSO-$d_6$) $\delta$(ppm):
2.60(3H,s), 3.72(2H,bs), 4.45(2H,bs),
5.22(1H,d,J=5Hz), 5.38(2H,bs), 5.85(1H,bs),
6.92(1H,s), 7.17(1H,s), 7.27(1H,s), 8.20(1H,s),
8.50(1H,s), 9.80(1H,s).
IR(KBr): $\nu_{C=O}$ 1780 cm$^{-1}$.

2.0 g of the above trifluoroacetate was suspended in 60 ml of water, and dissolved with an addition of 2.2 g of sodium hydrogencarbonate. Insolubles were removed by filtration, and the aqueous layer was washed with 20 ml of n-butanol. The aqueous layer was separated.

The separated aqueous layer was adjusted to pH 3.5 by an addition of 1N hydrochloric acid, and formed precipitates were collected by filtration and washed sequentially with water, ethyl ether and acetone, and then added to a solution of 150 mg of sodium hydrogencarbonate in 15 ml of water, then freeze-dried to obtain 1.0 g of a sodium salt of the above identified compound.

We claim:

1. A cephalosporin compound having the formula:

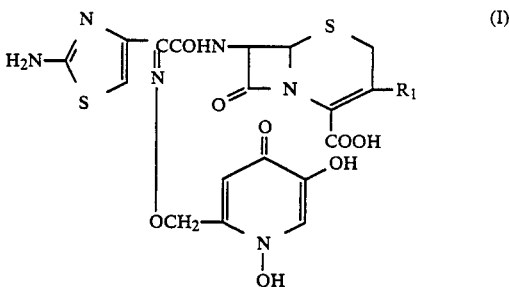

wherein $R_1$ is —CH$_2$—A wherein A is tetrazolyl, thiazolylthio, isothiazolylthio, thiadiazolylthio, triazolylthio, triazinylthio, tetrazxolylthio, triazolylpyrimidinylthio, pyridinium-4-ylthio or 2,3-cyclopentenopyridinium-4-ylthio group which is unsubstituted or substituted hby one to three groups selected from the group consisting of a $C_{1-4}$ alkyl group, a carboxymethyl group, a $C_{1-4}$ alkoxycarbonylmethyl group, a hydroxy-($C_{1-4}$)alkyl group, a di-($C_{1-4}$)alkylamino-($C_{1-4}$)alkyl group, a carboxyl group, a hydroxyl group, an oxo group and an amino group, or a pharmaceutically acceptable salt thereof.

2. (6R, 7R)-7-[(Z)-2-(2-aminothiazol-4-yl)-2-(1,5-dihydroxy-4-pyridon-2-ylmethoxyimino)acetamido]-3-(1,2,3-thiadiazol-5-ylthiomethyl)-3-cephem-4-carboxylic acid or a pharmaceutically acceptable salt thereof, according to claim 1.

3. (6R, 7R)-7-[(Z)-2-(2-aminothiazol-4-yl)-2-(1,5-dihydroxy-4-pyridon-2-ylmethoxyimino)acetamido]-3-[1-(2-hydroxyethyl)-1H-tetrazol-5-ylthiomethyl]-3-cephem-4-carboxylic acid or a pharmaceutically acceptable salt thereof, according to claim 1.

4. (6R, 7R)-7-[(Z)-2-(2-aminothiazol-4-yl)-2-(1,5-dihydroxy-4-pyridon-2-ylmethoxyimino)acetamido]-3-(1-methylpyridinium-4-ylthiomethyl)-3-cephem-4-carboxylate, according to claim 1.

5. (6R, 7R)-7-[(Z)-2-(2-aminothiazol-4-yl)-2-(1,5-dihydroxy-4-pyridon-2-ylmethoxyimino)acetamido]-3-(5-methyl-s-triazolo[1,5-a]pyrimidin-7-ylthiomethyl)-3-cephem-4-carboxylic acid or a pharmaceutically acceptable salt thereof, according to claim 1.

6. An antibacterial pharmaceutical composition containing an antibacterially effective amount of a cephalosporin compound of the formula I as defined in claim 1 or a pharmaceutically acceptable salt thereof.

7. A method of treating infectious disease which comprises administering an antibacterially effective amount of a cephalosporin compound of the formula I as defined in claim 1 to an animal or human being.

* * * * *